(12) United States Patent
Gordon et al.

(10) Patent No.: US 11,311,384 B2
(45) Date of Patent: Apr. 26, 2022

(54) METHOD FOR PERFORMING SINGLE-STAGE CRANIOPLASTY RECONSTRUCTION WITH A CLEAR CUSTOM CRANIOFACIAL IMPLANT

(71) Applicant: Longeviti Neuro Solutions LLC, Hunt Valley, MD (US)

(72) Inventors: Chad R. Gordon, Cockeysville, MD (US); Jesse Christopher, Hunt Valley, MD (US); Bradley Rabinovitz, Annapolis, MD (US)

(73) Assignee: LONGEVITI NEURO SOLUTIONS LLC, Hunt Valley, MD (US)

( * ) Notice: Subject to any disclaimer, the term of this patent is extended or adjusted under 35 U.S.C. 154(b) by 249 days.

(21) Appl. No.: 16/291,624

(22) Filed: Mar. 4, 2019

(65) Prior Publication Data

US 2019/0192298 A1 Jun. 27, 2019

Related U.S. Application Data

(63) Continuation-in-part of application No. 15/957,325, filed on Apr. 19, 2018, now Pat. No. 10,835,379.

(Continued)

(51) Int. Cl.
*A61F 2/28* (2006.01)
*A61B 17/80* (2006.01)
(Continued)

(52) U.S. Cl.
CPC .......... *A61F 2/2875* (2013.01); *A61B 17/688* (2013.01); *A61B 17/8061* (2013.01); *A61F 2/30942* (2013.01); *A61B 2017/00907* (2013.01); *A61B 2017/00924* (2013.01); *A61B 2034/105* (2016.02); *A61B 2034/108* (2016.02); *A61F 2002/2882* (2013.01);
(Continued)

(58) Field of Classification Search
None
See application file for complete search history.

(56) References Cited

U.S. PATENT DOCUMENTS 5,545,226 A 8/1996 Wingo et al.
5,902,326 A 11/1999 Lessar et al.
(Continued)

FOREIGN PATENT DOCUMENTS

EP 2680787 A1 1/2014
WO WO2012047759 A1 4/2012
(Continued)

OTHER PUBLICATIONS

Aatman M. Shah, Henry Jung, and Stephen Skirboll, Materials used in cranioplasty: a history and analysis, Apr. 2014, pp. 1-7, Neurosurg Focus, vol. 26. DOI: 10.3171/2014.2.FOCUS13561.
(Continued)

*Primary Examiner* — David H Willse
(74) *Attorney, Agent, or Firm* — Welsh Flaxman & Gitler LLC

(57) ABSTRACT

A method for performing a cranioplasty includes the steps of prefabricating a sonolucent craniofacial implant based upon information generated by preoperative scans, creating a cranial, craniofacial, and/or facial defect, and attaching the craniofacial implant to the cranial, craniofacial, and/or facial defect. The craniofacial implant is composed of a material that is sonolucent and exhibits attenuation of less than 6 dB/cm.

21 Claims, 26 Drawing Sheets

Related U.S. Application Data

(60) Provisional application No. 62/489,036, filed on Apr. 24, 2017.

(51) Int. Cl.
  *A61F 2/30* (2006.01)
  *A61B 17/68* (2006.01)
  *A61B 34/10* (2016.01)
  *A61B 17/00* (2006.01)

(52) U.S. Cl.
  CPC ............ *A61F 2002/3009* (2013.01); *A61F 2002/3096* (2013.01); *A61F 2002/30948* (2013.01)

(56) References Cited

U.S. PATENT DOCUMENTS

| | | | |
|---|---|---|---|
| 6,112,109 | A | 8/2000 | D'Urso |
| 6,932,842 | B1 | 8/2005 | Litschko et al. |
| 7,747,305 | B2 | 6/2010 | Dean et al. |
| 8,086,336 | B2 | 12/2011 | Christensen |
| 8,775,133 | B2 | 7/2014 | Dean et al. |
| D723,162 | S | 2/2015 | Brogan et al. |
| 9,044,195 | B2 | 6/2015 | Manwaring et al. |
| 9,101,341 | B2 | 8/2015 | Fitzgerald et al. |
| 9,592,124 | B2 | 3/2017 | Joganic |
| 9,883,944 | B2 | 2/2018 | Batty et al. |
| 9,901,268 | B2 | 2/2018 | Hughes et al. |
| 9,901,269 | B2 | 2/2018 | Hu et al. |
| 2006/0224242 | A1 | 10/2006 | Swords et al. |
| 2007/0038100 | A1 | 2/2007 | Nita |
| 2012/0259428 | A1 | 10/2012 | Brogan et al. |
| 2013/0282011 | A1 | 10/2013 | Brogan et al. |
| 2013/0345599 | A1 | 12/2013 | Lin et al. |
| 2015/0105858 | A1 | 4/2015 | Papay et al. |
| 2016/0184100 | A1 | 6/2016 | Joganic |
| 2016/0185046 | A1 | 6/2016 | Littlefield |
| 2016/0193048 | A1 | 7/2016 | Prada |
| 2016/0296312 | A1 | 10/2016 | Kuhn et al. |
| 2017/0156596 | A1 | 1/2017 | Aguilar-Mendoza et al. |
| 2017/0273797 | A1 | 9/2017 | Gordon et al. |
| 2017/0274102 | A1 | 9/2017 | Lim et al. |
| 2017/0365054 | A1 | 12/2017 | Dean et al. |
| 2017/0368330 | A1 | 12/2017 | Silay et al. |
| 2018/0042725 | A1 | 2/2018 | Antonyshyn et al. |
| 2018/0055640 | A1 | 3/2018 | Gordon et al. |

FOREIGN PATENT DOCUMENTS

| | | |
|---|---|---|
| WO | WO2012116401 A1 | 9/2012 |
| WO | 2018064239 A1 | 4/2018 |
| WO | 2018154477 A1 | 8/2018 |

OTHER PUBLICATIONS

A.E. Abdulai, M.I. Iddrissu and T.K. Dakurah, Cranioplasty Using Polymethyl Methacrylate Implant Constructed from an Alginate Impression and Wax Elimination Technique, Mar. 2006, pp. 18-21, vol. 40, No. 1, Ghana Medical Journal.

L.C. Hieu, E. Bohez, J. Vander Sloten, P. Oris, H.N. Phien, E. Vatcharaporn and P.H. Binh, Design and manufacturing of Cranioplasty Implants by 3-axis CNC Milling, Feb. 20, 2002, pp. 1-11, Technology and Health Care, IOS Press.

Gordon et al., "First In-Human Experience With Complete Integration of Neuromodulation Device Within a Customized Cranial Implant," Operative Neurosurgery (Oct. 6, 2017).

Fuller et al., "Real Time Imaging with the Sonic Window: A Pocket-Sized, C-Scan, Medical Ultrasound Device," 2009 IEEE International Ultrasonic Symposium Proceedings.

Tobius et al., "An ultrasound window to perform scanned, focused ultrasound hyperthermia treatments of brain tumors," Med. Phys. 14(2), Mar./Apr. 1987.

Caro-Osorio, E. et al. (2013). Cranioplasty with polymethylmethacrylate prostheses fabricated by hand using original bone flaps: Technical note and surgical outcomes. Surg Neurol Int., 4, 136. https://doi.org/10.4103/2152-7806.119535.

METHOD FOR PERFORMING SINGLE-STAGE CRANIOPLASTY RECONSTRUCTION WITH A CLEAR CUSTOM CRANIOFACIAL IMPLANT

CROSS REFERENCE TO RELATED APPLICATION

This application is a continuation-in-part of U.S. patent application Ser. No. 15/957,325, filed Apr. 19, 2018, entitled "METHOD FOR PERFORMING SINGLE-STAGE CRANIOPLASTY RECONSTRUCTION WITH A CLEAR CUSTOM CRANIAL IMPLANT," which issued as U.S. Pat. No. 10,835,379, which claims the benefit of U.S. Provisional Patent Application Ser. No. 62/489,036, filed Apr. 24, 2017, entitled "METHOD FOR PERFORMING SINGLE-STAGE CRANIOPLASTY RECONSTRUCTION WITH A CLEAR CUSTOM CRANIAL IMPLANT."

BACKGROUND OF THE INVENTION

1. Field of the Invention

The present invention generally relates to the field of surgery. In particular, the invention relates to the brain and skull, the art of reconstructing skull defects (i.e., cranioplasty), neurosurgery, neurology, neuroplastic and reconstructive surgery, and craniofacial plastic surgery.

2. Description of the Related Art

Craniectomies requiring skull reconstruction (i.e., cranioplasty) are often indicated for a multitude of etiologies including decompression (i.e., skull removal) following stroke or traumatic brain injury, bone flap infection (i.e., osteomyelitis) and/or bone flap resorption following previous neurosurgery, and/or oncological ablation for masses involving the underlying brain and/or skull. In the setting of traumatic brain injuries with cerebral edema, stroke (i.e., brain ischemia) with bleeding, and/or autologous bone flap resorption or osteomyelitic infections requiring removal, delayed cranioplasties are necessary at a secondary stage.

In fact, nearly 250,000 primary brain tumors/skull-based neoplasms are diagnosed each year resulting in a range of 4,500-5,000 second-stage implant cranioplasties per year (Berli J U, et al., "Immediate Single-Stage Cranioplasty Following Calvarial Resection for Benign and Malignant Skull Neoplasms Using Customized Craniofacial Implants," The Journal of Craniofacial Surgery, Vol. 26, No. 5, September 2015).

The common types of cranial implants used today, in instances where the exact bone defect shape and size is known well in advance, are made most often from a variety of safe biomaterials (i.e. manmade), including titanium mesh, porous hydroxyapatite (HA), polymethylmethacrylate (PMMA), porous polyethylene, and polyether-ether-ketone (PEEK), among others. Of note, the most common "off-the-shelf" solution used by neurosurgeons and reconstructive surgeons is titanium mesh implants bent to serve as a "bridge"—simply spanning the skull defect from one side to another to create a non-specific curvature and protection barrier for the brain. The thin titanium mesh (which is 1 millimeter thick versus the normal skull thickness of 4-5 millimeters) accompanies several drawbacks and limitations including 1) non-anatomical thickness and secondary deadspace underneath, 2) a need to overlap neighboring skull areas for bridging and stability which can lead to visible deformities, pain, and/or scalp irregularities within the anterior craniofacial regions (i.e., non-hair bearing regions), and 3) a high risk of extrusion through the scalp when placed under thin and/or irradiated scalps. Ultimately, such mesh implants exhibit major differences in thickness and texture when compared to the resected anatomy of the patient.

A distinct subset of skull reconstruction patients includes craniectomy defects following oncological resection of calvarial lesions and/or brain tumors invading the skull. For this type of tumor ablative surgery, where tumors and/or processes (i.e., radiation therapy) involve the skull, cranioplasties to date have previously been performed using either 1) suboptimal hand-molding techniques with "off-the-shelf" products" or 2) a delayed, second surgery allowing the design and fabrication of a customized cranial implant. Now, with the advent of computer-aided design/manufacturing (CAD/CAM) and customized craniofacial implants, more suited alternatives are becoming widely available and have been published (Berli J U, et al., "Immediate Single-Stage Cranioplasty Following Calvarial Resection for Benign and Malignant Skull Neoplasms Using Customized Craniofacial Implants," The Journal of Craniofacial Surgery, Vol. 26, No. 5, September 2015).

Using CAD/CAM fabrication, near-perfectly shaped custom cranial implants can be ordered and pre-fabricated with exact patient-specific curvatures to an oversized dimension, and then modified around the edges intra-operatively for an exact fit following bone/brain tumor resection as described by Gordon et al. (See, Gordon C R, et al., "Discussion of Usefulness of an Osteotomy Template for Skull Tumorectomy and Simultaneous Skull Reconstruction," The Journal of Craniofacial Surgery, Vol. 27, No. 6, September 2016; Berli J U, et al., "Immediate Single-Stage Cranioplasty Following Calvarial Resection for Benign and Malignant Skull Neoplasms Using Customized Craniofacial Implants," The Journal of Craniofacial Surgery, Vol. 26, No. 5, September 2015.)

To accomplish this approach, preoperative imaging such as computed tomography (CT) is used ahead-of-time to identify the patient's exact skull and brain anatomy and the patient's exact skull curvature (since all patients have different curvatures based on region, gender, and age). However, the exact cranial or craniofacial defect size (following oncological resection) is truly unknown until the final tumor and local disease extension are removed to completion with visual confirmation—since in some instances, there is tumor extension into neighboring regions (i.e., bone, brain) unseen on pre-operative imaging which then requires a more extensive resection than originally planned. As such, for one to follow true oncological principles and to make sure the surgeon is unrestricted in removing all concerning areas of disease (thereby decreasing all risk of recurrence), the prefabricated custom implant must be designed with extraneous material around the edges (but at the same time with the exact curvature specific to the patient's missing anatomy)—to be able to accommodate the unexpected tumor size and whether or not a larger size is needed, as opposed to what was originally imagined. Therefore, the pre-operative CT scan images are used to virtually plan the surgical skull cuts in an oversized fashion around the bone/brain tumor with excess of several inches (up to 5 to 7 centimeters, on average, of excess implant material) based on the tumor's exact location (and to allow the geometric design of the three-dimensional (3D) custom cranial implant to be created in an "oversized fashion"). But as opposed to the current "off-the-shelf" products mentioned previously, this customized implant made of a safe biomaterial remains advantageous since it's "patient-specific" with respect to the individual's exact craniofacial convexity and curvature equating to minimal-to-no deformity after surgery.

In summary, the "single-stage cranioplasty" method and pre-fabricated custom implant with excess dimensions, described here, is designed to account for any additional bone/soft tissue loss that may become necessary to remove during the surgery (that is, due to unanticipated local brain or skull invasion, desire to decrease risk of recurrence and enlargement of resection limits, an unknown tumor pathology grade until resected and sent for frozen analysis with pathology, etc.). Therefore, after resecting the bony/soft tissue region of interest, the surgeon is forced to shave down and modify the oversized custom cranial or craniofacial implant to fit exactly within the resected area using artistic hand-eye coordination, dedicate significant time and labor intra-operatively (up to 80 minutes), and work back and forth in the operating room between the patient's final anatomy and a sterile back table to achieve an ideal fit, as described by Berli J U, et al. ("Immediate Single-Stage Cranioplasty Following Calvarial Resection for Benign and Malignant Skull Neoplasms Using Customized Craniofacial Implants," The journal of Craniofacial Surgery, Vol. 26, No. 5, September 2015). Similarly, a surgeon could remove normal bone in order to place an intercranial device above an area of brain pathology amenable to local intervention, as described by Gordon et al. in International Patent Application PCT/US2016/030447, filed May 2, 2017, entitled "LOW PROFILE INTERCRANIAL DEVICE," (published as WO 2017/039762) ('762 Publication), which is incorporated herein by reference.

As such, current techniques for modifying the oversized custom cranial implant for "single-stage cranioplasty" are inefficient and far from optimal given the abundant amount of time and artistic labor needed to perform "back-and-forth" size modification with a handheld burr. With significant operative times being extended, the patient's perioperative morbidity is increased as well as are the fixed operating rooms costs surrounding prolonged surgery. Therefore, newer strategies have been developed and described for instance using "opaque" customized implants, such as disclosed in the inventor's own U.S. Patent Application Publication No. 2017/0000505, entitled "Computer-Assisted Craniomaxillofacial Surgery."

Still further, the current market only offers these opaque (or non-clear) cranial implants (described in U.S. Patent Application Publication No. 2017/0000505) with zero visibility and zero translucency—which is a significant deterrent to the neurosurgeon or reconstructive craniofacial surgeon hoping to perform single-stage cranioplasty. With the abundant availability of only "opaque" implants, on the current market, there is increased complexity and artistic demand challenging all surgeons when faced with this difficult scenario. These demands are demonstrated in FIGS. 1A-G and FIGS. 2A-G which show a cranioplasty performed with an opaque cranial implant. As the pictures show, the procedure requires hand-modification following skull tumor resection of either a brain tumor (as shown in FIGS. 1A-G) or skull tumor (as shown in FIGS. 2A-G), and its difficulty is exponentially increased. The hand modification is highly difficult due to the inability to see through the implant and NOT being able to appreciate the underlying skull margins underneath when placed in-situ. Of note, one can appreciate the unintentional perimeter defects secondary to one's ability to not see clearly through the implant—which is related to either "undershaving" or "overshaving" the implant's borders—as a way to make the oversized implant fit. Whether improper sizing results in "undershaving" or "overshaving," both types of error detract from the final reconstructive result. For example, undershaving leaves the implant too small and increases risk for resulting deformity. But in an ideal setting, a "clear" customized cranial implant (made of a safe biomaterial with complete translucency) would be a much welcomed advance to the fields of neurosurgery and skull reconstruction—both to lower accompanying complexity and to drastically quicken the operation.

Accordingly, a surgical method that allows surgeons to resize, adjust, modify or trim alloplastic or bio-engineered cranial implants during cranioplasty (i.e., skull reconstruction) surgery to fit the surgical cuts, defects, and/or preexisting deformities in a streamlined fashion with reduced complexity, operative time, and/or demand for artistic hand-eye coordination, or generally overcome the limitations of current technology and surgical methods, described here, would be welcome in the art. While Gordon et al. have previously developed surgical methods method, techniques and systems using a robot-assisted and/or laser-assisted method as described in U.S. Patent Application Publication No. 2017/0000505, these novel technologies were developed solely based on the assumption that one would be forced to use the commonly-available, "opaque" customized cranial implants. Thus, up until this time, there have been no developments taking advantage of specific implant biomaterials that are clear and/or newfound implant translucency in the manner disclosed and claimed in accordance with the present invention.

Further still, both non-invasive and invasive transcranial ultrasound have demonstrated numerous therapeutic/diagnostic applications including neuromodulation for movement disorders, magnetic resonance imaging (MRI)-guided lesion ablation, and local drug delivery via blood brain barrier disruption. Unfortunately however, these emerging technologies remain limited by the acoustic properties of cranial bone causing ultrasonic wave attenuation, scattering and absorption. Hersh D S, Kim A J, Winkles J A, Eisenberg H M, Woodworth G F, Frenkel V. Emerging Applications of Therapeutic Ultrasound in Neuro-oncology: Moving Beyond Tumor Ablation. *Neurosurgery.* 2016; 79(5):643-654; Christian E, Yu C, Apuzzo M L J. Focused ultrasound: relevant history and prospects for the addition of mechanical energy to the neurosurgical armamentarium. *World Neurosurg.* 2014; 82(3-4):354-365; Quadri S A, Waqas M, Khan I, et al. High-intensity focused ultrasound: past, present, and future in neurosurgery. *Neurosurg Focus.* 2018; 44(2):E16; Weintraub D, Elias W J. The emerging role of transcranial magnetic resonance imaging guided focused ultrasound in functional neurosurgery. *Mov Disord.* 2017; 32(1):20-27; Carpentier A, Canney M, Vignot A, et al. Clinical trial of blood-brain barrier disruption by pulsed ultrasound. *Sci Transl Med.* 2016; 8(343):343re2; Gutierrez M I, Penilla E H, Leija L, Vera A, Garay J E, Aguilar G. Novel Cranial Implants of Yttria-Stabilized Zirconia as Acoustic Windows for Ultrasonic Brain Therapy. *Adv Healthc Mater.* 2017; 6(21); Monteith S, Sheehan J, Medel R, et al. Potential intracranial applications of magnetic resonance-guided focused ultrasound surgery. *J Neurosurg.* 2013; 118(2):215-221; Vignon F, Shi W T, Yin X, Hoelscher T, Powers J E. The stripe artifact in transcranial ultrasound imaging. *J Ultrasound Med* 2010; 29(12):1779-1786; Pinton G, Aubry J-F, Bossy E, Muller M, Pernot M, Tanter M. Attenuation, scattering, and absorption of ultrasound in the skull bone. *Med Phys.* 2012; 39(1):299-307.

Single-stage cranioplasty presents a newfound opportunity for neurosurgeons to create a synthetic acoustic window by replacing normal bone with a cranial implant composed of sonolucent biomaterial, a material providing minimal to no obstruction of ultrasonic waves. A sonolucent cranial implant would thereby permit "trans-cranioplasty ultrasound" (TCU) for both diagnostic and therapeutic postoperative applications. Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. (anticipated publication 2019).

SUMMARY OF THE INVENTION

It is, therefore, an object of the present invention to provide a method for performing a cranioplasty including the steps of prefabricating a sonolucent craniofacial implant based upon information generated by preoperative scans, creating a cranial, craniofacial, and/or facial defect, and attaching the craniofacial implant to the cranial, craniofacial, and/or facial defect.

It is also an object of the present invention to provide a method for performing a cranioplasty wherein the craniofacial implant is composed of PMMA.

It is another object of the present invention to provide a method for performing a cranioplasty including the step of performing intraoperative ultrasound imaging through the craniofacial implant.

It is further an object of the present invention to provide a method for performing a cranioplasty including the step of performing postoperative ultrasound imaging through the craniofacial implant.

It is also an object of the present invention to provide a method for performing a cranioplasty wherein the step of creating a cranial, craniofacial, and/or facial defect includes cutting out a portion of a skull to be replaced with the craniofacial implant.

It is another object of the present invention to provide a method for performing a cranioplasty wherein a neurological device with constant or intermittent function is incorporated within the craniofacial implant.

It is further an object of the present invention to provide a method for performing a cranioplasty wherein the cranioplasty is a single-stage cranioplasty.

It is also an object of the present invention to provide a method for performing a cranioplasty wherein the cranial, craniofacial, and/or facial defect is created in the pterional region.

It is another object of the present invention to provide an implant comprising a craniofacial implant composed of a material that is sonolucent and exhibits attenuation of less than 6 dB/cm.

It is further an object of the present invention to provide an implant wherein the craniofacial implant is a custom craniofacial implant.

It is also an object of the present invention to provide an implant wherein the custom craniofacial implant is generated by preoperative scans.

It is another object of the present invention to provide an implant wherein craniofacial implant is composed of PMMA.

It is further an object of the present invention to provide an implant wherein craniofacial implant is shaped and dimensioned for performance of pterional craniotomies.

It is also an object of the present invention to provide an implant wherein craniofacial implant includes an outer flat first surface, an inner second surface, and a peripheral edge extending between the outer flat first surface and the inner second surface.

It is another object of the present invention to provide an implant wherein the outer flat first surface has a length of at least 35 mm in both the X and Y directions of a plane in which the outer flat first surface lies so as to be slightly wider than a transducer.

It is further an object of the present invention to provide an implant wherein craniofacial implant includes an outer first surface, an inner concave second surface, and a peripheral edge extending between the outer first surface and the inner concave second surface.

It is also an object of the present invention to provide an implant wherein the inner concave second surface is shaped to maintain contact with a dura for optimizing optical coupling with the dura.

It is another object of the present invention to provide an implant wherein craniofacial implant includes an outer flat first surface, an inner concave second surface, and a peripheral edge extending between the outer flat first surface and the inner concave second surface.

It is further an object of the present invention to provide an implant wherein the inner concave second surface is shaped to maintain contact with a dura for optimizing optical coupling with the dura.

It is also an object of the present invention to provide an implant wherein the outer flat first surface has a length of at least 35 mm in both the X and Y directions of a plane in which the outer flat first surface lies so as to be slightly wider than a transducer.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 3A-3G, 4A, and 4B illustrate together a schematic representative of the present method for single-stage cranioplasty reconstruction using a clear craniofacial implant and the final result with the embedded final clear craniofacial implant, wherein FIGS. 3A-3G show the steps from a single-stage cranioplasty reconstruction in accordance with the present invention and FIGS. 4A and 4B respectively show pre-operative (left) and post-operative (right) CT scans showing a large left sided skull tumor and post-resection views exhibiting ideal symmetry and optimal implant location using a clear custom cranial implant in accordance with the present invention.

In particular, FIG. 3A shows cutting out the diseased portion of the skull or that portion of the skull required to access diseased tissue of the brain or other portion of the anatomy, and thereby creating a cranial, craniofacial, and/or facial defect.

In particular, FIG. 3B shows a perspective view and a top plan view of the removed portion of the skull.

In particular, FIG. 3C shows positioning the prefabricated clear custom craniofacial implant over the cranial, craniofacial, and/or facial defect created by the removal of the diseased anatomical feature.

In particular, FIG. 3D shows tracing cut lines with a hand-held sterile marker on the prefabricated clear custom craniofacial implant as it lies in-situ over the cranial, craniofacial, and/or facial defect.

In particular, FIG. 3E shows cutting the prefabricated clear custom craniofacial implant along the tracing cut lines for optimal fit of the prefabricated clear custom craniofacial implant along the cranial, craniofacial, and/or facial defect and to create the final-size/shape of clear craniofacial implant for exact fit.

FIG. 3F shows an optional step of robot-assisted trimming of the prefabricated clear custom craniofacial implant along the tracing cut lines.

In particular, FIG. 3G shows attaching the final clear craniofacial implant to the patient with tumor pathology with cranial bone.

In particular, FIG. 4A is a pre-operative CT scan with tumor pathology with cranial bone.

In particular, FIG. 4B is a post-operative CT scan with ideal cranioplasty result and optimal symmetry of both hard and soft tissue.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1A:
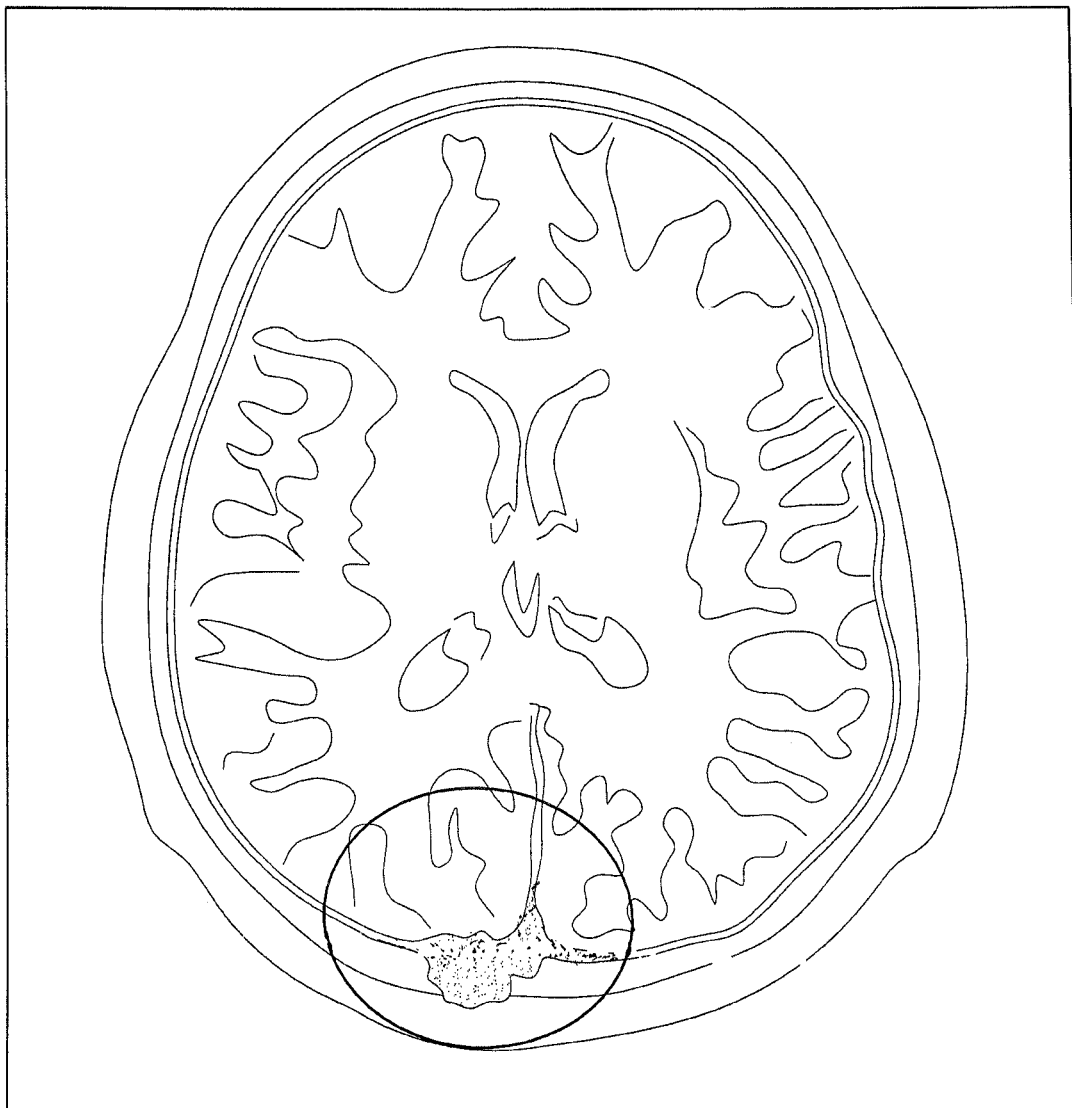
FIGS. 1A-G show a cranioplasty performed with an opaque cranial implant, wherein the cranioplasty is a result of a brain tumor (for example, see the axial CT scan image of FIG. 1A showing brain tumor invasion into the skull and the bird's eye view of FIG. 1B showing the same appearance of a normal scalp despite the brain tumor invading into the skull).
Figure 1B:
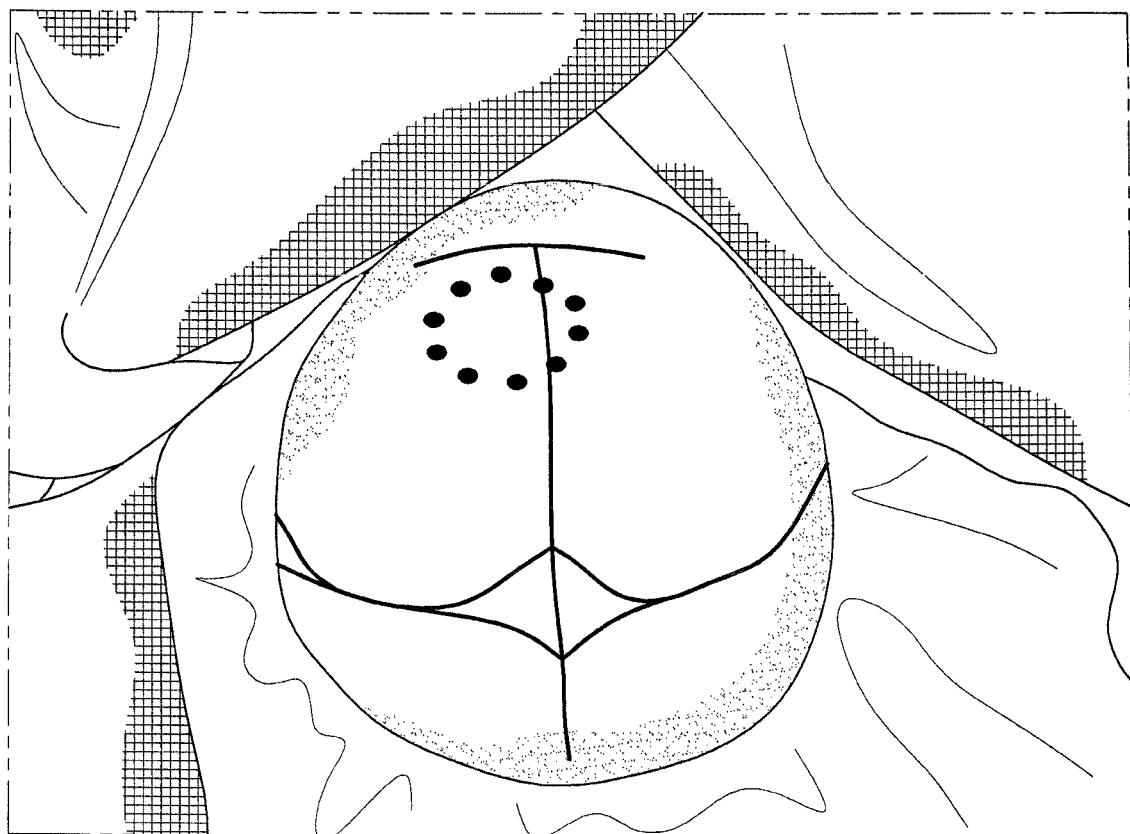
Figure 1C:
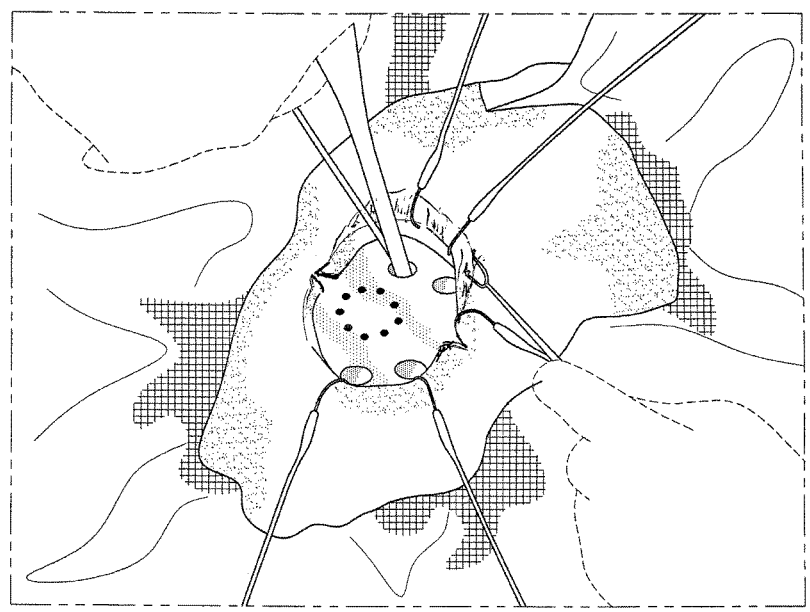
Figure 1D:
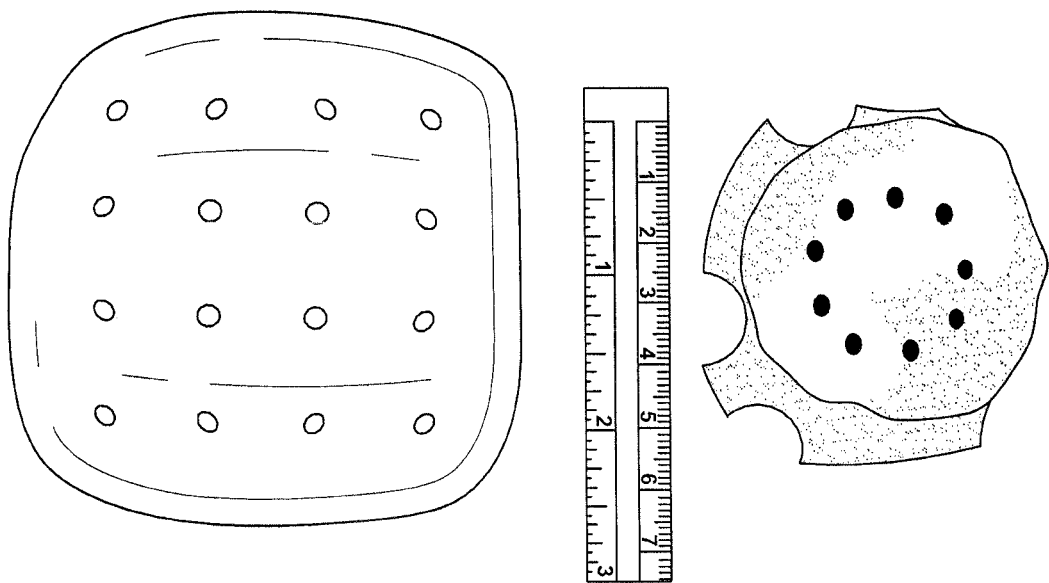
Figure 1E:
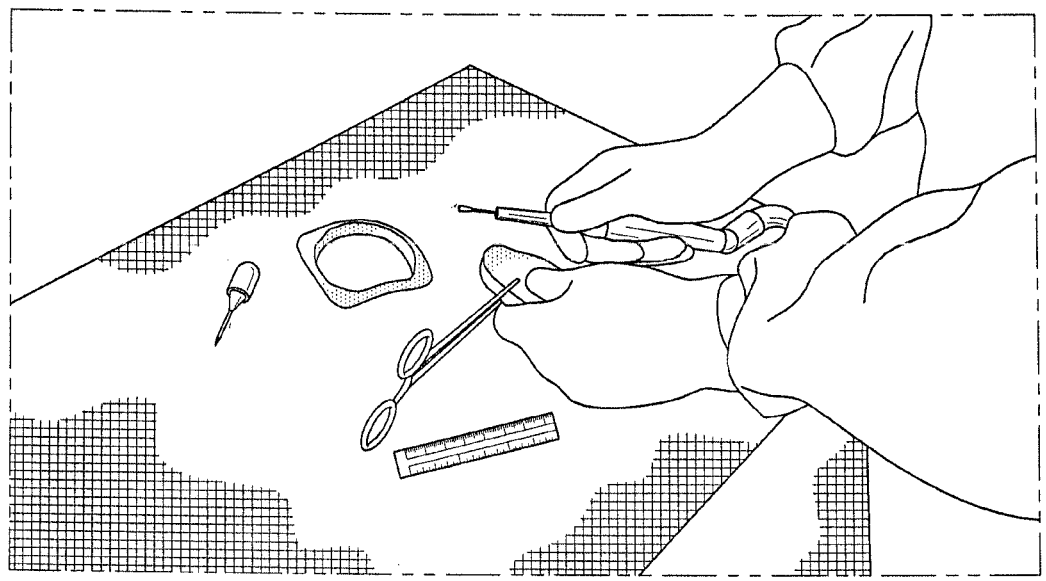
Figure 1F:
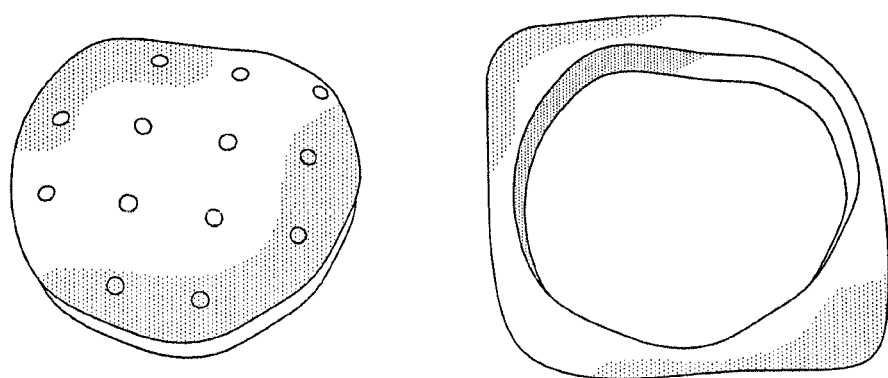
Figure 1F:
Figure 1G:
Figure 2A:
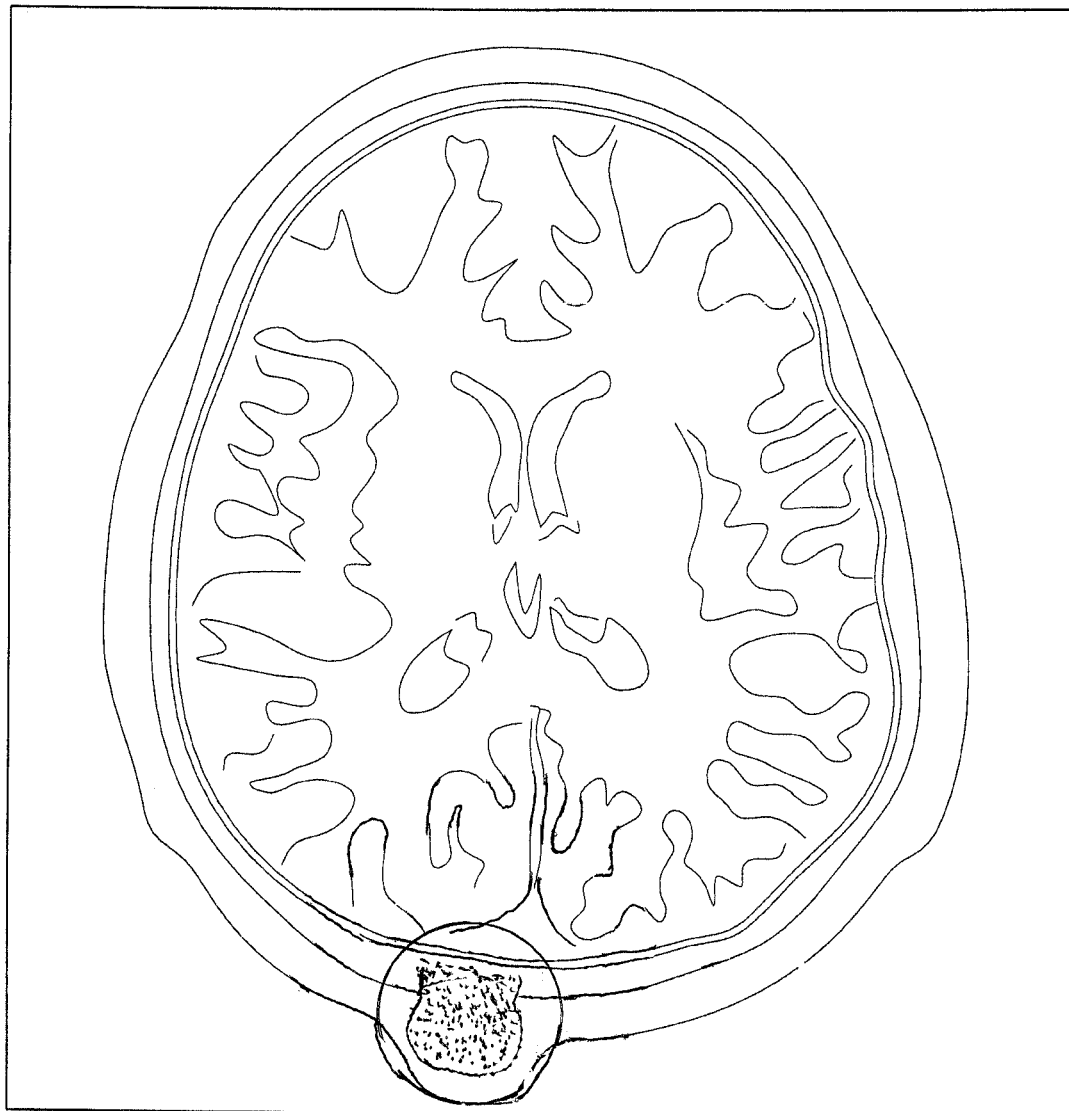
FIGS. 2A-G show a cranioplasty performed with an opaque cranial implant, wherein the cranioplasty is a result of a skull tumor (for example, see the axial CT scan image of FIG. 2A showing skull tumor protruding outwardly from the skull and the bird's eye view of FIG. 2B showing the outward protuberance along the scalp resulting from the skull tumor extending outwardly from the skull).
Figure 2B:
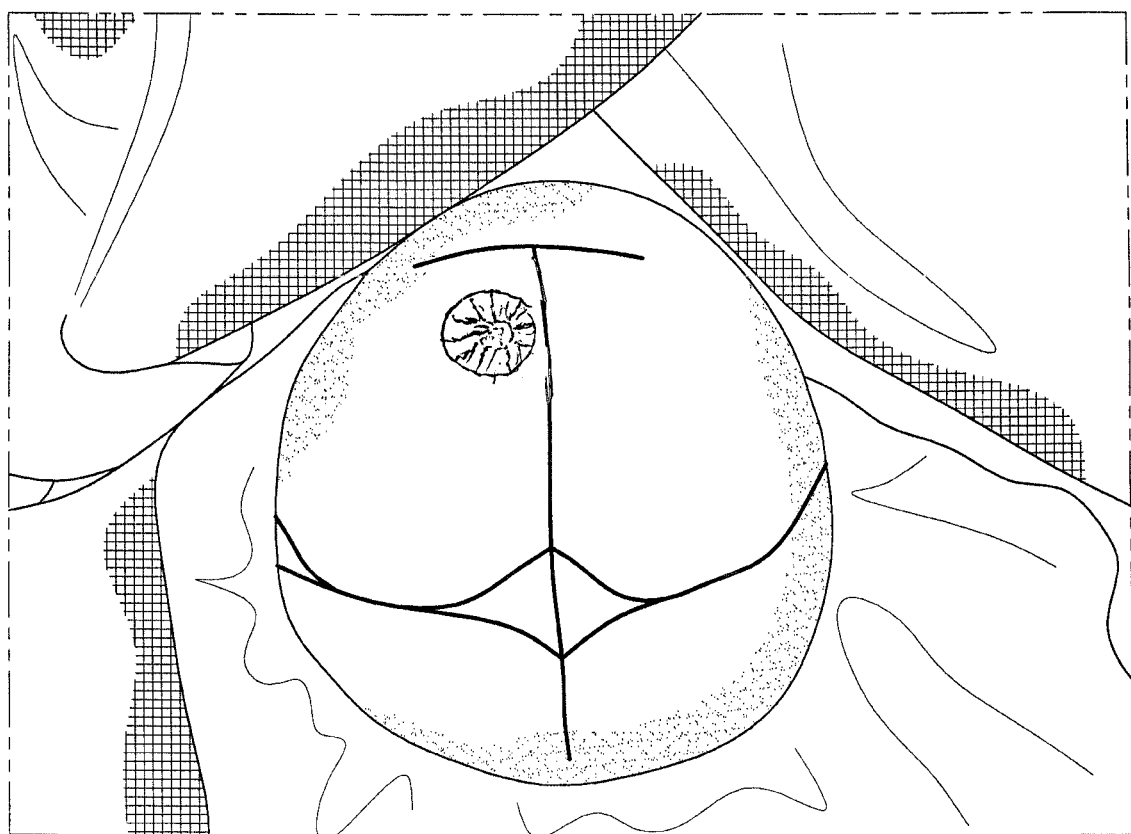
Figure 2C:
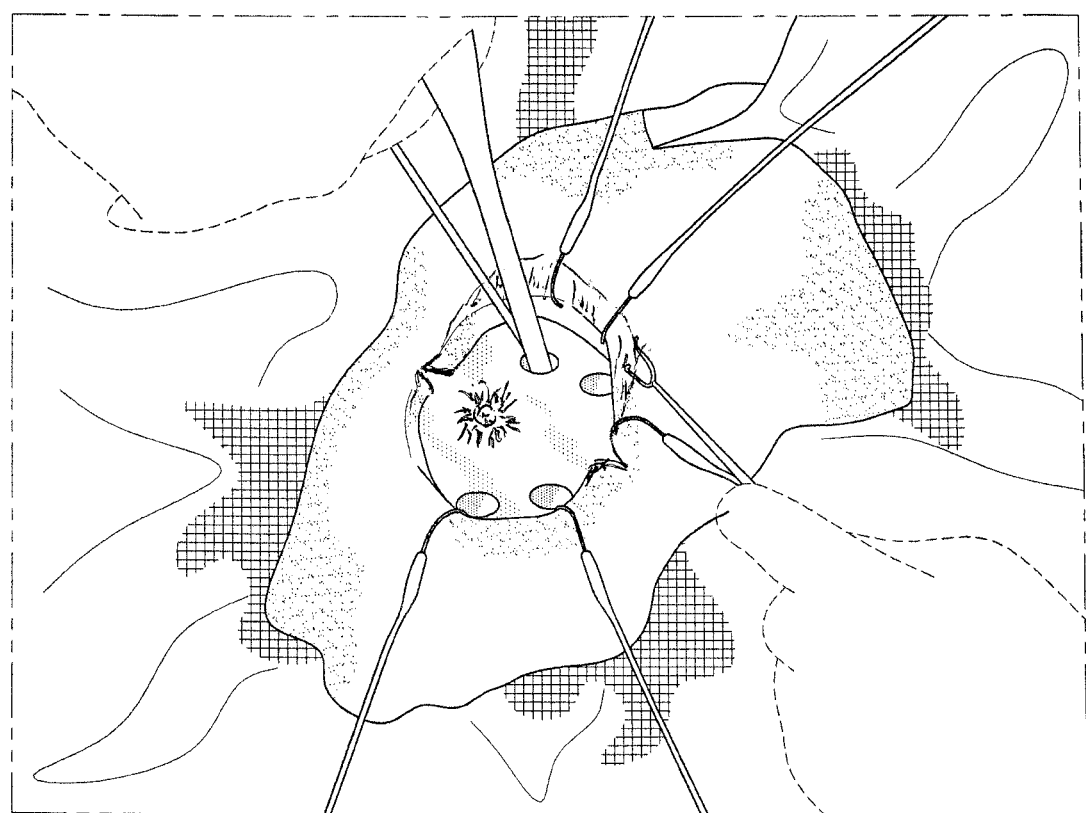
Figure 2D:
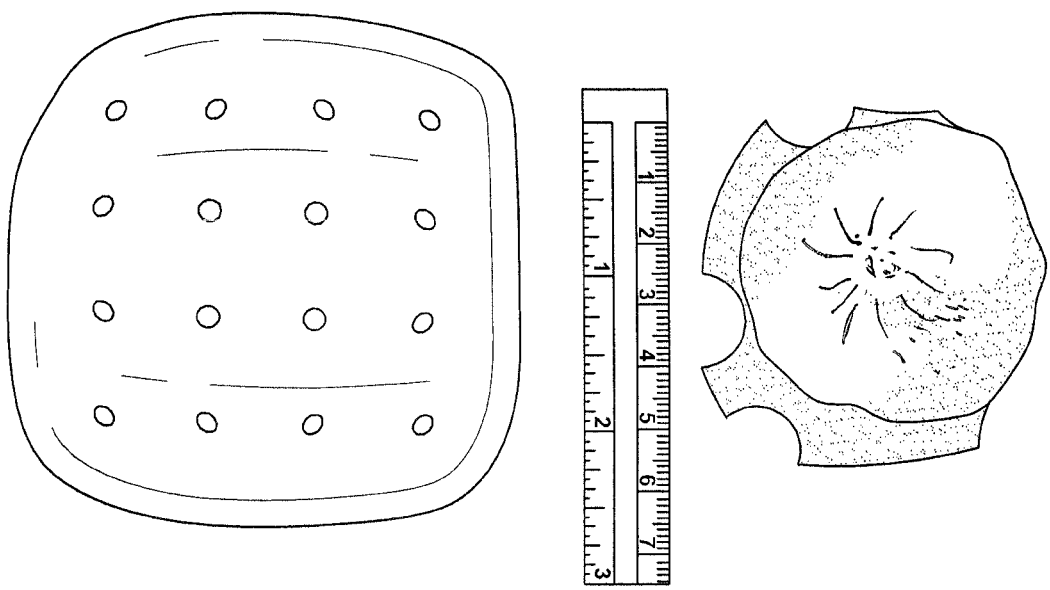
Figure 2E:
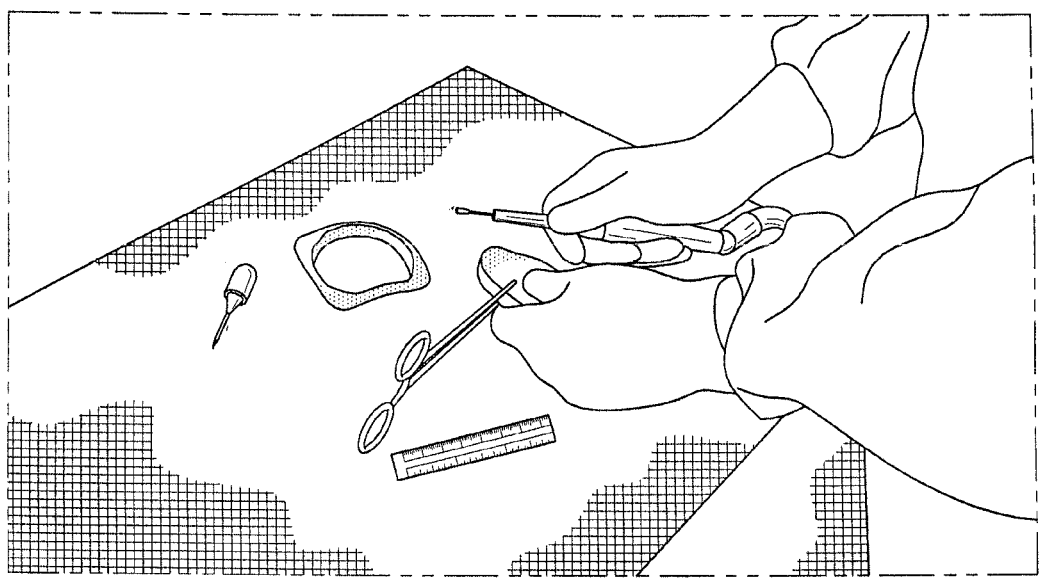
Figure 2F:
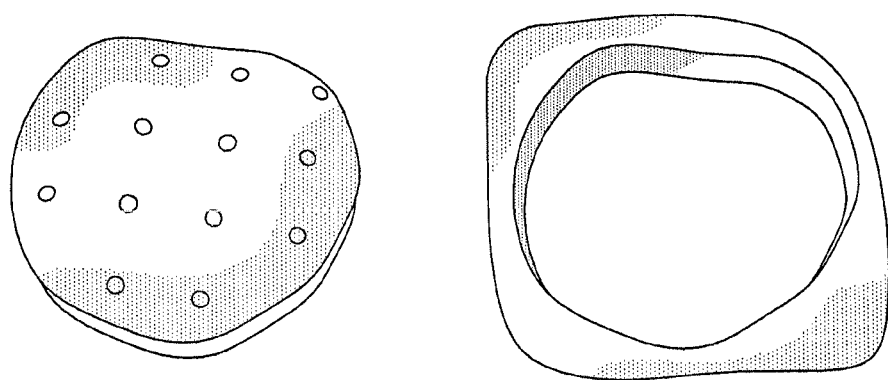
Figure 2F:
Figure 2G:
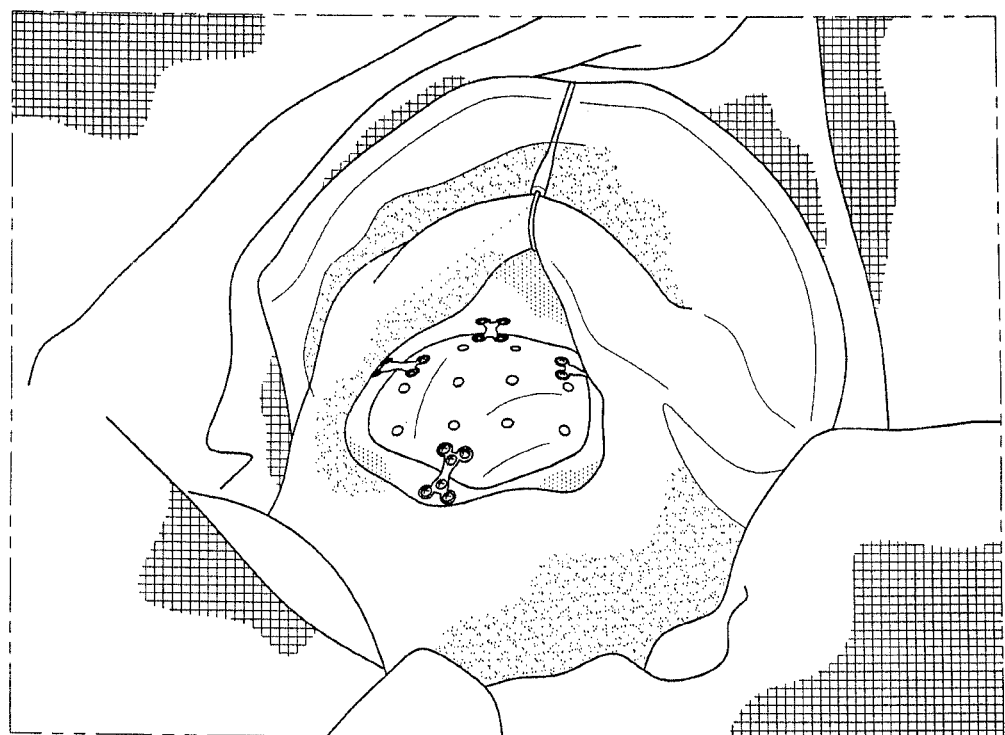
Figure 3A:
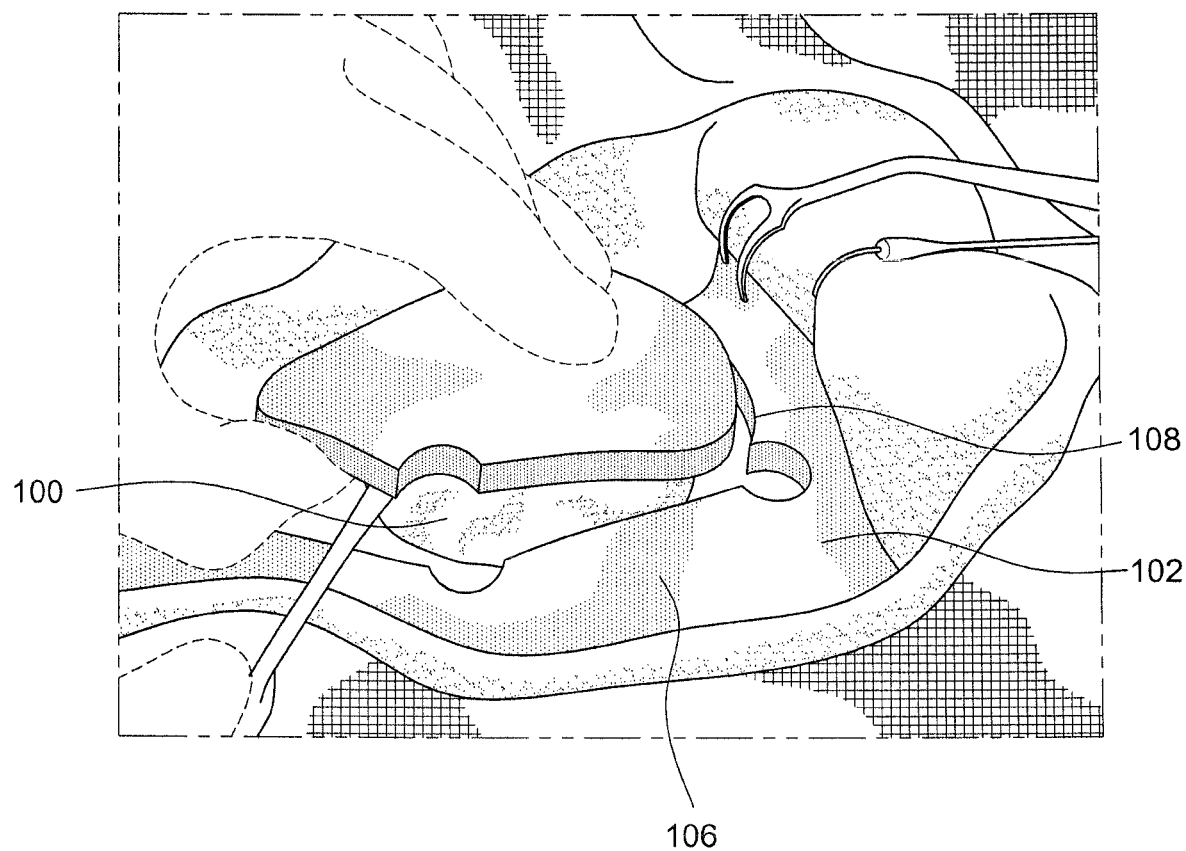
Figure 3B:
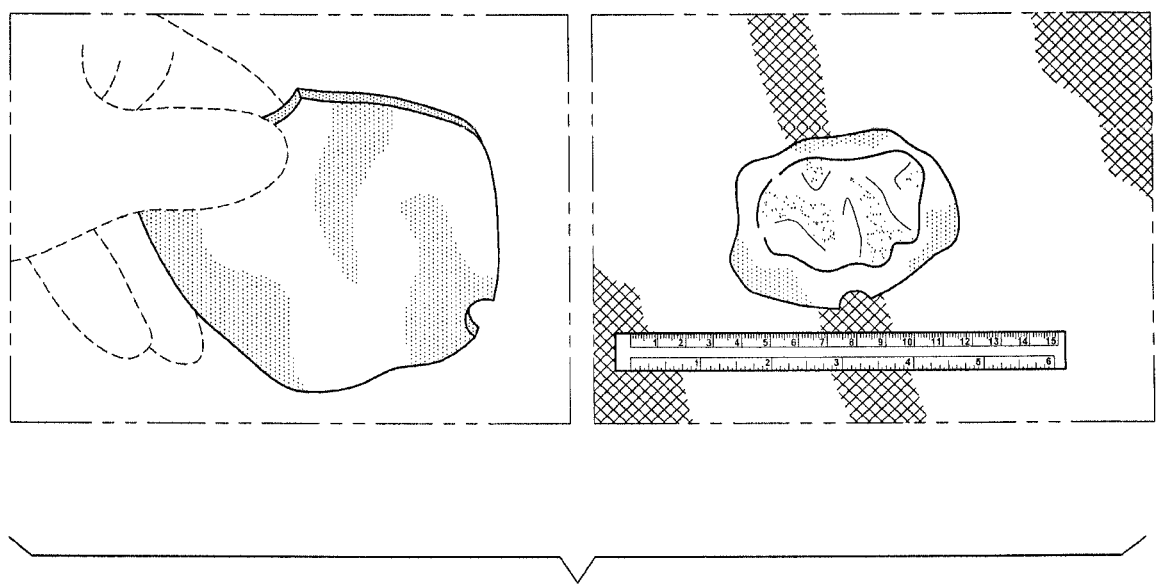
Figure 3C:
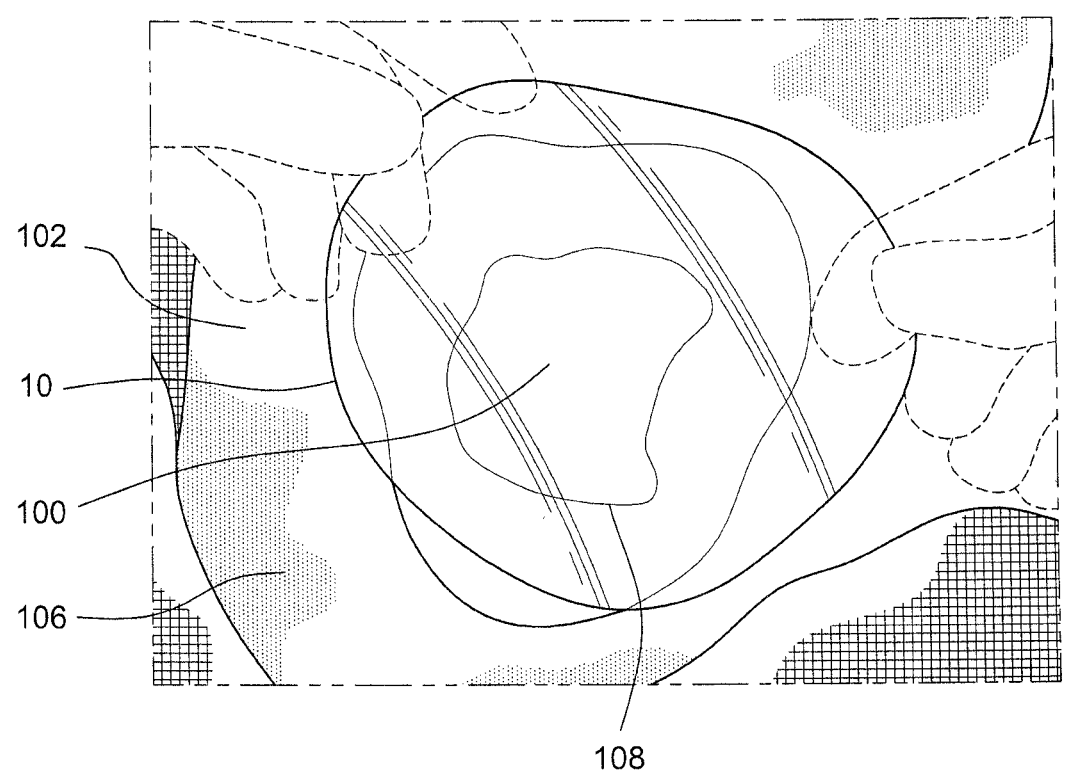
Figure 3D:
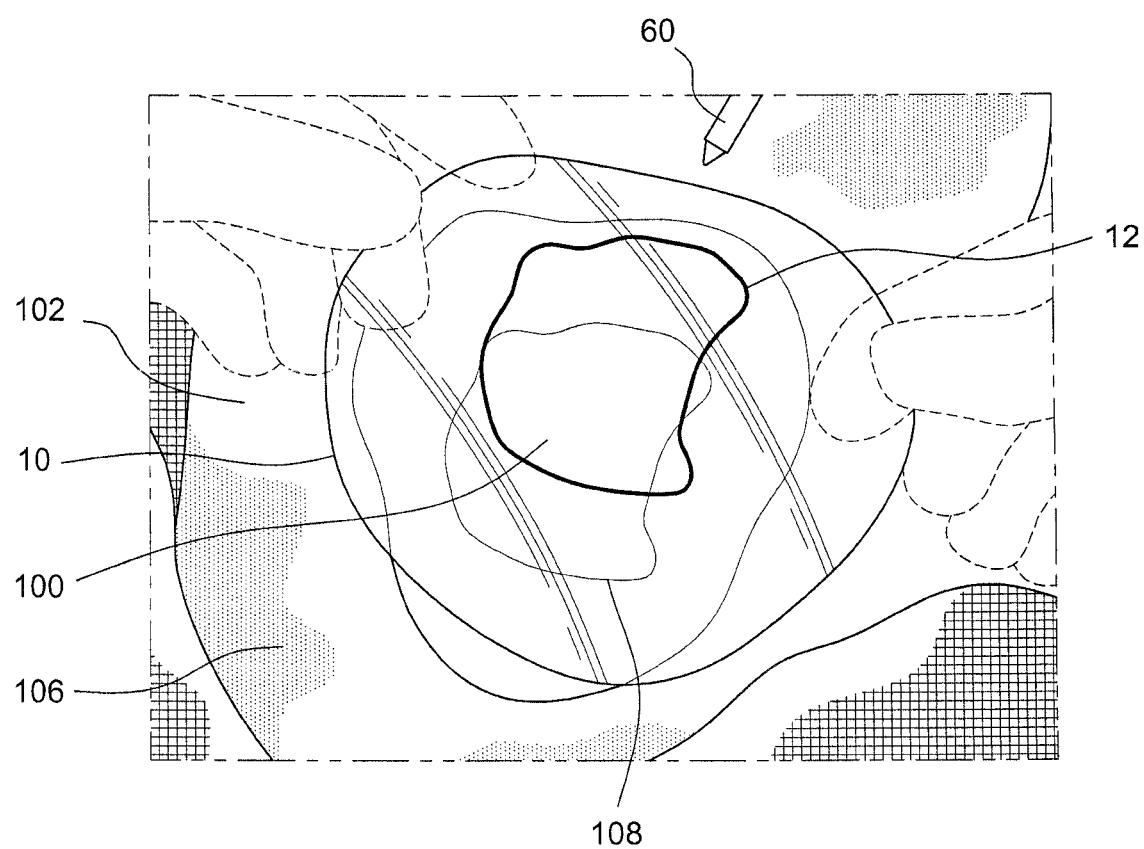
Figure 3E:
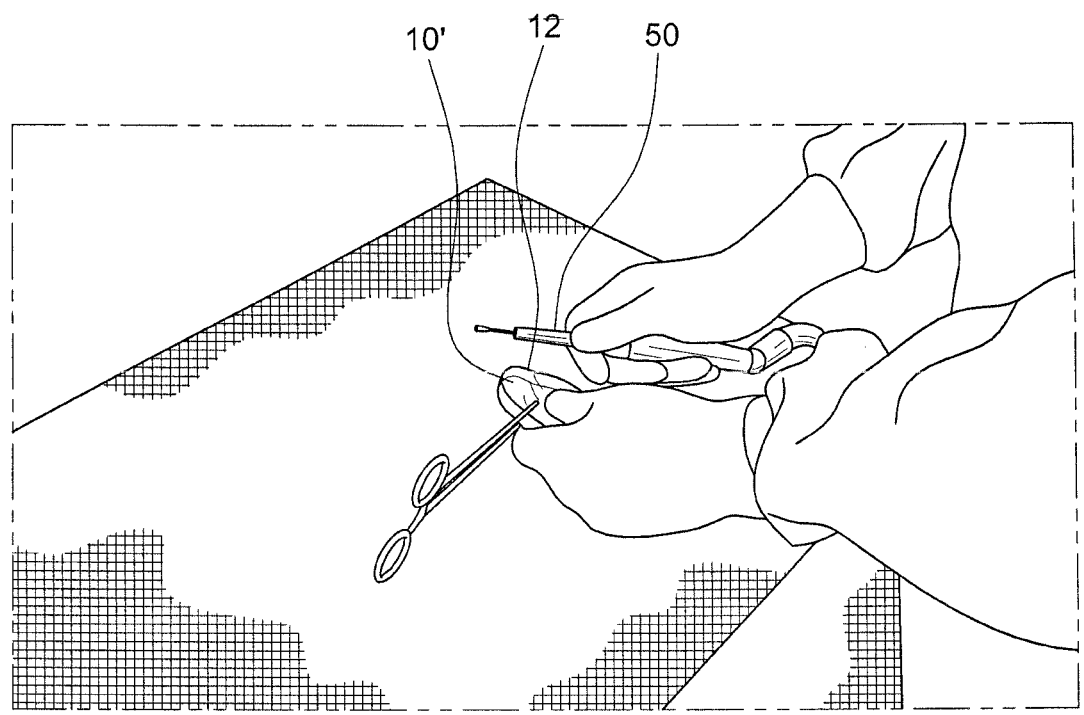
Figure 3F:
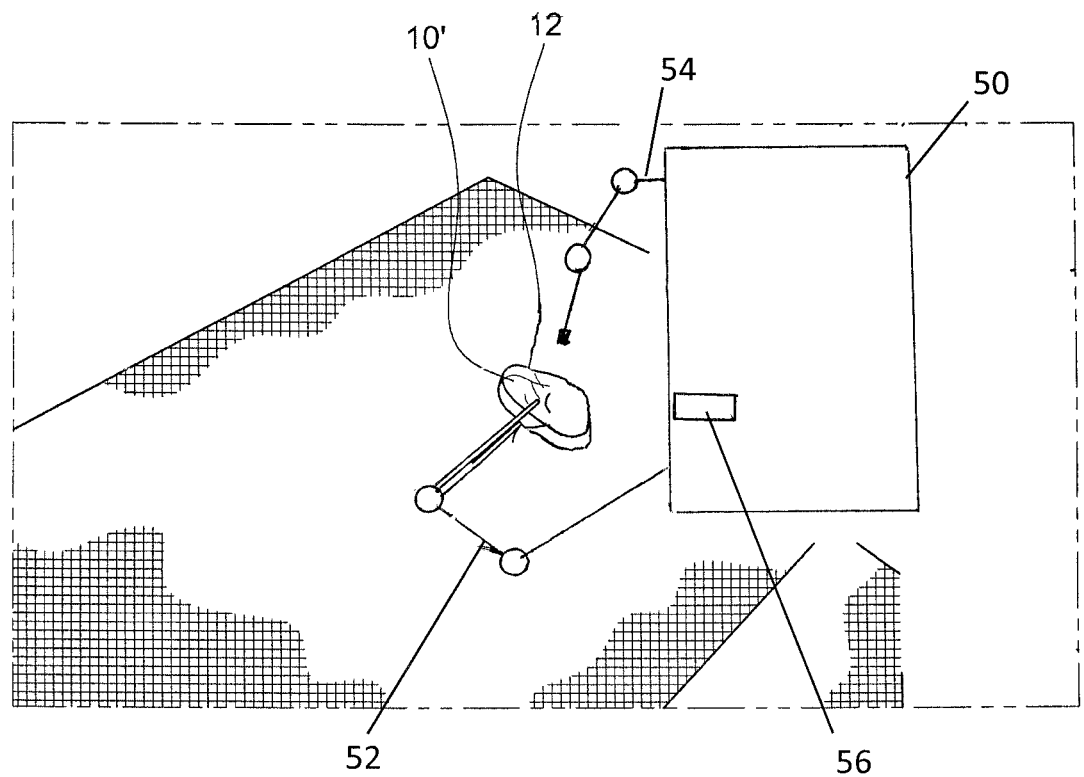

Referring to FIGS. 3A-3G, 4A, 4B, and 5, the present invention relates to a novel method for performing single-stage cranioplasty with "clear" customized implants (see for example, FIGS. 3C and 3D showing the clear custom craniofacial implant 10 held directly above a skull tumor defect following extirpation (that is, the cranial, craniofacial, and/or facial defect 100 as discussed below) prior to single-stage modification). As explained above in the Background of the Invention, the method of "single-stage cranioplasty" is defined as a surgery where the surgeon intends to create a complicated, full-thickness, three-dimensional defect in the craniofacial skeleton in real-time and then replace the subsequent craniofacial bone (and/or soft tissue) with an oversized patient-specific custom implant requiring on-table size modification—versus using an "off-the-shelf" biomaterial with no form or curative match of customization specific to the patient's anatomy. Or, this could be applicable to situations when the surgeon is notified of an upcoming case with little notice and does not have time to obtain other types of skull implants which may take more time to manufacture, like those made of porous polyethylene, for example. Furthermore, clear implants for single-stage cranioplasty also accompany a significant advantage of seeing the brain anatomy underneath during the case which allows for critical viewing of watertight dural closure, dural pulsations, and/or potential bleeding sources, such as the tumor cavity or sagittal sinus, for example. As such, this novel "translucency" of the clear custom craniofacial implant 10 equates to both a safer, and more effective, method for single-stage cranioplasty.

In accordance with the present invention, and as will be explained below in greater detail, the present invention makes use of prefabricated custom craniofacial implants 10 made of a "clear" translucent material, man-made alloplastic or other tissue engineered material, to allow and improve a surgeon's ability to view a cranial, craniofacial, and/or facial defect 100, and brain anatomy distal (i.e., underneath) to the prefabricated clear custom craniofacial implant 10 when placed into an overlapping position (see FIGS. 3A-3G, 4A, and 4B showing a single-stage cranioplasty reconstruction in accordance with the present invention) relative to the cranial, craniofacial and/or cranial defect 10). In accordance with the single-stage cranioplasty reconstruction shown in FIGS. 3A-3G, 4A, and 4B involving a large skull tumor and clear custom implant 10 the two distinct advantages of the present invention are depicted—one being streamlined customization (that is, using human vision as opposed to needing computer assisted or robot assisted methods as previously detailed by Gordon et al.), and the other being critical viewing of brain-related structures for potential cerebrospinal fluid leak and/or bleeding risk during the case.

Of note, one can appreciate the minimal perimeter defects seen at time of inset following intra-operative size modification of a "clear" customized craniofacial implant 10—which required only 8 total minutes for real-time, size modification. The reduced time and final outcome is completely related to the enhanced value of the implant's clear translucency—and the required time is about 90% less when compared to the previous cases described by the inventor's team in instances of using an opaque implant. By allowing the surgeon to see through the prefabricated "clear" custom craniofacial implant 10 and directly view the cranial, craniofacial, and/or facial defect 100 and brain anatomy over which the craniofacial implant 10 is to be positioned, the surgeon can save significant time and effort in matching the cranial, craniofacial, and/or facial defect 100 directly to the prefabricated clear custom craniofacial implant 10, without the use of multiple estimations or templates. Seeing through the clear custom craniofacial implant 10 also allows the surgeon to choose where to reshape the prefabricated clear custom craniofacial implant 10 and form the final clear craniofacial implant 10' that will ideally fit the cranial, craniofacial, and/or facial defect 100. This newfound advantage of complete clarity and enhanced visibility through the craniofacial implant 10 described herein provides several unprecedented advantages specific to "single-stage cranioplasty," including 1) ease-of-use with drastic reduction in operative times, 2) a new found ability to provide real-time visibility to pertinent anatomy underneath like exact bone edge dimensions dictating implant size modification, 3) the potential to discover brain-related bleeding cerebrospinal fluid leakage underneath which requires electrocautery/suturing and can help to prevent re-operations related to post-operative leaking/bleeding, and 4) visualize periodic dural pulsations suggestive of healthy brain parameters follow tumor resection. As such, this invention drastically reduces the time needed for reshaping and matching the prefabricated clear custom craniofacial implant 10 by around ten-fold, which now ranges between 8 and 10 minutes in some instances performed by the inventor, Dr. Gordon (instead of up to 80 minutes, as reported by Berli et al, J Craniofacial Surgery Vol. 26, No. 5, September 2015).

As those skilled in the art will appreciate, and as mentioned above, prefabricated custom craniofacial implants manufactured for reconstruction are inherently larger than the cranial, craniofacial, and/or facial defect created during surgery to adequately fill the cranial, craniofacial, and/or facial defect, but shall retain the exact curvature of a patients missing anatomy. In accordance with a preferred embodiment of the present invention, the clear custom craniofacial implant 10 with full transparency is a prefabricated implant such as a 3rd-party sourced alloplastic or tissue-engineered implant, preferably manufactured from clear poly(methyl methacrylate) (PMMA) or any other clear biocompatible material suited for safe use in craniofacial reconstruction. While a clear PMMA craniofacial implant is used in accordance with a preferred embodiment as discussed herein, it is appreciated the prefabricated clear custom craniofacial implant 10 may include a polymer, metal, bioengineered material, or any combinations thereof for which may also be clear. For example, the prefabricated clear custom craniofacial implant 10 may include any biomaterial that may allow enhanced visibility with complete translucency. In addition, it is appreciated the use of the term craniofacial implant herein is intended to include all clear implants that may be used in conjunction with skull reconstruction procedures, facial reconstruction, or any combination thereof. Regardless of the material construction employed in the fabrication of the clear prefabricated custom craniofacial implant, the implant must be completely translucent to provide the advantages described herein, which include 1) decreased operative times since underlying anatomy is assessed in superimposed fashion, 2) decreased blood loss for patient since the implant reconstruction is completed much faster, 3) decreased anesthesia and operative times, 4) decreased costs to hospital since surgery is abbreviated, and 5) reduced demand for artistic, hand-eye coordination, additional labor and/or work effort provided by the reconstructive surgeon. As used herein the term "clear" is intended to refer to a material that is substantially completely transparent (for example, the craniofacial implant is completely transparent with the exception of a neurological device(s) that might be integrated into the craniofacial implant and which does not otherwise impede the ability to achieve the underlying principles of the invention) and exhibits the property of transmitting rays of light through its substance so that bodies situated beyond or behind can be distinctly seen when looking through the material. In addition, to being optically transparent, it is appreciated additional advantages are achieved by making the implant from material that allows for the transmission of ultrasound, Bluetooth signals, etc., alone or in combination.

In addition to the direct advantages associated with the single-stage cranioplasty reconstruction, the craniofacial implant being "translucent" also allows for real-time transmission of light, which is critical for future applications related to any and all battery-powered, low-profile intercranial devices capable of neuromodulation (i.e. implanted functional RNS systems like NeuroPace) and capable of sending wireless electrocorticography (ECoG) signals for data collection, interpretation, treatment, and intervention; and a multitude of other wavelength-related mediums like optical coherence tomography (OCT) imaging and ultrasound imaging—as described by Gordon et al in International Patent Application PCT/US2016/030447, filed May 2, 2016 entitled "LOW PROFILE INTERCRANIAL DEVICE" (published as WO 2017/039762), and U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANUFACTURED THEREBY" (published as U.S. Patent Application Publication No. 2018/0055640), which claims the benefit of U.S. Provisional Patent Application 62/381,242, filed Aug. 30, 2016, entitled "METHOD FOR MANUFACTURING A LOW-PROFILE INTERCRANIAL DEVICE AND THE LOW-PROFILE INTERCRANIAL DEVICE MANUFACTURED THEREBY," all of which are incorporated herein by reference. In addition, Dr. Gordon and team published a "first in-human" experience article related to this novel invention (Gordon C, et al, "First In-Human Experience With Complete Integration of Neuromodulation Device Within a Customized Cranial Implant," Operative Neurosurgery 2017; 10 (6): 1-7). Further still, ultrasound imaging is discussed in Belzberg M, Ben Shalom N, Yuhanna E, Manbachi A, Tekes A, Huang J, Brem Ii, Gordon C, "Sonolucent Cranial Implants: Cadaveric study and Clinical Findings Supporting Diagnostic and Therapeutic Trans-Cranioplasty Ultrasound," J Craniofac Surg. (anticipated publication 2019).

Figure 3G:
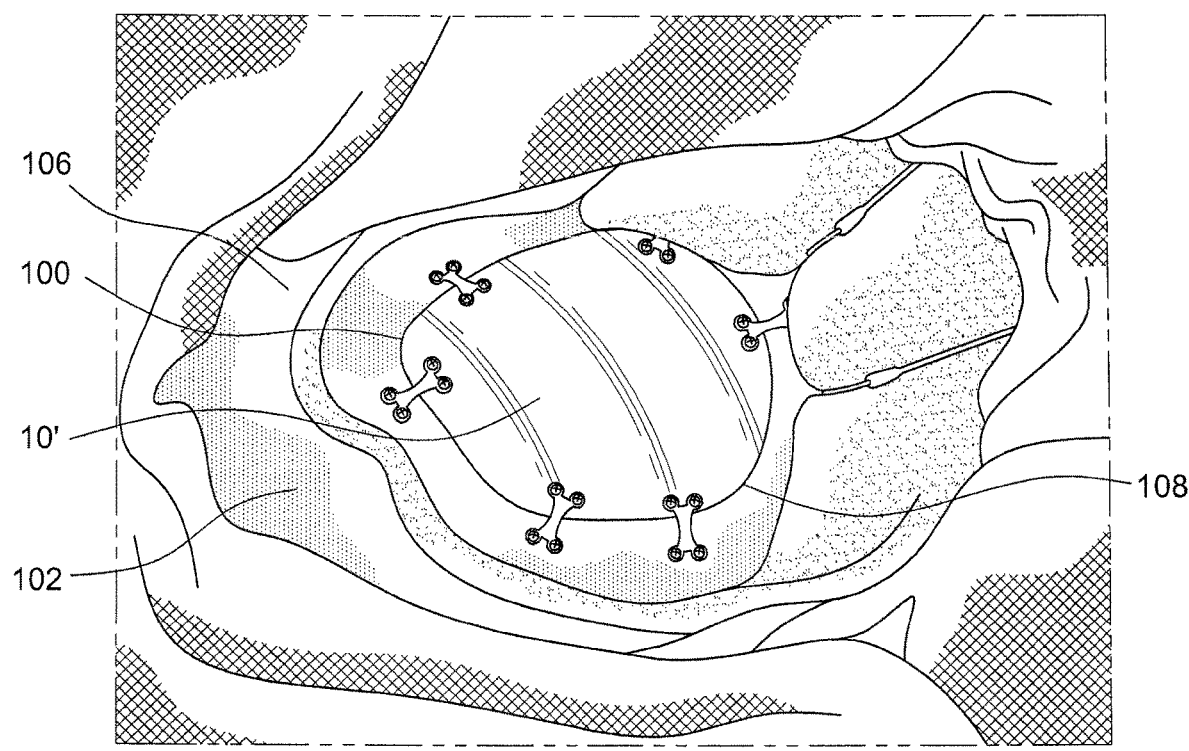

As those skilled in the art will appreciate single-stage implant cranioplasty involves the surgical rebuilding and/or reconstruction of portions of the craniomaxillofacial skeleton to correct deformities (e.g., following trauma) and/or defects with unanticipated dimensions created in real-time—such as those involving tumor extirpation. Preoperative imaging such as CT or MRI identifies the patient anatomy. The surgery is planned using virtual pre-operative imaging to help identify an area of disease (e.g., the tumor) requiring resection and reconstruction. In addition to identifying diseased portions of the craniofacial anatomy, diseased portions of the brain anatomy may be identified and addressed in the implantation of an intercranial device(s) including neurotechnology 20 with constant or intermittent function as described in the '762 Publication (see, for example, FIG. 5) wherein the intercranial device is substantially clear and functions in the same manner as the clear custom craniofacial implant 10 described herein. Such neurological devices 20 include, but are not limited to, hydrocephalus shunt valve/pressure monitor, direct medicine delivery device, microchip polymer delivery device, radiation therapy device, functional neuromodulation device, etc. See, for example, Gordon C, Wolff A, Santiago G, Liebman K, Veznedaroglu E, Vrionis F, Huang j, Brem H, Luciano M, "First-in-Human Experience With Integration of a Hydrocephalus Shunt Device Within a Customized Cranial Implant," Operative Neurosurgery (anticipated publication 2019). Bony cuts are planned and the prefabricated clear custom craniofacial implant 10 is designed to fit into the resected region following planned modification of the prefabricated clear custom craniofacial implant 10 (that is, the creation of the final clear craniofacial implant 10'). See, for example, FIG. 3G showing the clear custom craniofacial implant with ideal fit in place following tumor resection and optimal reconstruction, and with minimal gaps along skull-implant interface and reduced operative time.

Still further, and considering the vast array of neurosurgical techniques and neurological devices that might be used in conjunction with the methodology underlying the present invention, the clear custom craniofacial implant may be manufactured to allow for the transmission of waves other than optical light waves, for example, the clear custom craniofacial implant may be sonolucent (that is, allowing passage of ultrasonic waves without production of echoes that are due to reflection of some of the waves) or radiolucent (that is, allowing passage of radio waves without production of echoes that are due to reflection of some of the waves). By way of example, the clear custom craniofacial implant 10 may be manufactured in a manner allowing for the transmission of ultrasonic waves as described in U.S. Pat. No. 9,044,195, entitled "IMPLANTABLE SONIC WINDOW," ('195 Patent) which is incorporated herein by reference. As explained in the '195 Patent, a strong, porous sonically translucent material through which ultrasonic waves can pass for purposes of imaging the brain is employed, wherein the material is a polymeric material, such as polyethylene, polystyrene, acrylic, or poly(methyl methacrylate) (PMMA). In addition, U.S. Pat. No. 9,535,192, entitled "METHOD OF MAKING WAVEGUIDE-LIKE STRUCTURES," ('192 Publication) and U.S. Patent Application Publication No. 2017/0156596, entitled "CRANIAL IMPLANTS FOR LASER IMAGING AND THERAPY," ('596 Publication) both of which are incorporated herein by reference, making waveguide-like structures within optically transparent materials using femtosecond laser pulses wherein the optically transparent materials are expressly used in the manufacture of cranial implants. The '596 publication explains the use of optically transparent cranial implants and procedures using the implants for the delivery of laser light into shallow and/or deep brain tissue. The administration of the laser light can be used on demand, thus allowing real-time and highly precise visualization and treatment of various pathologies. Further still, Tobias et al. describe an ultrasound window to perform scanned, focused ultrasound hyperthermia treatments of brain tumors. Tobias et al., "ULTRASOUND WINDOW TO PERFORM SCANNED, FOCUSED ULTRASOUND HYPERTHERMIA TREATMENTS OF BRAIN TUMORS," Med. Phys. 14(2), March/April 1987, 228-234, which is incorporated herein by reference. Tobias et al. tested various materials to determine which material would best serve as an acoustical window in the skull and ultimately determined polyethylene transmitted a larger percentage of power than other plastics and would likely function well as an ultrasonic window. Further still, Fuller et al., "REAL TIME IMAGING WITH THE SONIC WINDOW: A POCKET-SIZED, C-SCAN, MEDICAL ULTRASOUND DEVICE," IEEE International Ultrasonics Symposium Proceedings, 2009, 196-199, which is incorporated herein by reference, provides further information regarding sonic windows.

Radiolucency as applied to the present invention allows a clinician to see the anatomy surrounding the clear custom craniofacial implant 10 without "scatter" or interfering artifacts from the implant for diagnosis and follow-up. By another definition of radiolucency, radio waves are able to transmit easily through the clear custom craniofacial implant 10, for example, via Bluetooth or other frequency transmission; which can serve many purposes including, but not limited to, data management and controller telemetry. The provision of radiolucency also allows for the integration of markings (as discussed below) made with radiographic materials, for example, barium sulfate, to be visible in contrast to the remainder of the craniofacial implant to allow for unique device identifiers or unique patient information to be visible on post-operative scans.

Considering the provision of optical lucency in the present clear custom craniofacial implant 10, the ability to optically transmit through the clear custom craniofacial implant 10 allows for visualization of anatomy distal to the clear custom craniofacial implant 10 (as previously described), allows for the potential of higher bandwidth optical links (similar to radio transmission) between proximal adjunct devices, allows for light to be emitted from the clear custom craniofacial implant 10 to adjacent anatomy which could aid in optogenetics, and allows for imaging/therapeutic modalities that rely on light like optical coherence tomography from within the implant. Of note, this was shown to be true on a postoperative (day 5) cranioplasty patient with the clear implant. Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. (anticipated publication 2019).

In the newly described form of single-stage cranioplasty in accordance with the present invention, prior to surgery the prefabricated clear custom craniofacial implant 10 is ordered and delivered with oversized dimensions (several extra inches of material along the periphery) to account for additional bone or soft tissue that may be removed and needs to be replaced during the operation—and to, therefore, allow for trimming that is often necessary to optimize fit. After resecting the bony skull region of interest, the surgeon shaves down the oversized, prefabricated clear custom craniofacial implant 10 with a handheld burr to form the final clear craniofacial implant 10' that will have an exact fit within the resected area (that is, the cranial, craniofacial, and/or facial defect 100).

As will be appreciated based upon the following disclosure, the present method may be used for surgical repair of all cranial, craniofacial, and/or facial defects requiring large-size cranioplasty (e.g., >25 square centimeters). For example, embodiments described herein may be used for designing, forming, modifying and/or implanting clear custom craniofacial implants following benign/malignant skull neoplasm (tumor) resection or any form of bone disease requiring resection and visibility to pertinent anatomy underneath. Further, it is contemplated the present method may be used in order to implant an intercranial device, for example, as disclosed in the '762 Publication, above an area of brain pathology amenable to local intervention by the neurotechnology housed within the implant. Such an implantation of the present method would likely involve the removal of normal bone as opposed to diseased bone.

The present method provides for enhanced visualization related to a tumor, bone edges left behind, dura, brain pulsation, and any potential bleeding sources. The present invention further provides for enhanced visualization of the cranial, craniofacial, and/or facial defect 100 resulting from the removal of a portion of the skull to access the brain (or other tissue), and the reshaped final clear craniofacial implant 10' for exact positioning in place within the full-thickness defect of the skull. In other words, through the novel use of "clear" craniofacial implants in accordance with the present invention, the intraoperative execution of single-stage implant cranioplasties is improved and enhanced for ideal patient safety, streamlined execution with less time and effort, and reduced patient morbidity related to prolonged operative times. Furthermore, clear implants, such as those described here, contain all the necessary benefits for various implantable neurotechnologies such as neuromodulators, brain medicine delivery, hydrocephalus shunt valves, etc. Gordon C, et al, "First In-Human Experience With Complete Integration of Neuromodulation Device Within a Customized Cranial Implant," Operative Neurosurgery 2017; 10 (6): 1-7. Gordon C, Wolff A, Santiago G, Liebman K, Veznedaroglu E, Vrionis F, Huang J, Brem H, Luciano M, "First-in-Human Experience With Integration of a Hydrocephalus Shunt Device Within a Customized Cranial Implant," Operative Neurosurgery (anticipated publication 2019).

Figure 4A:
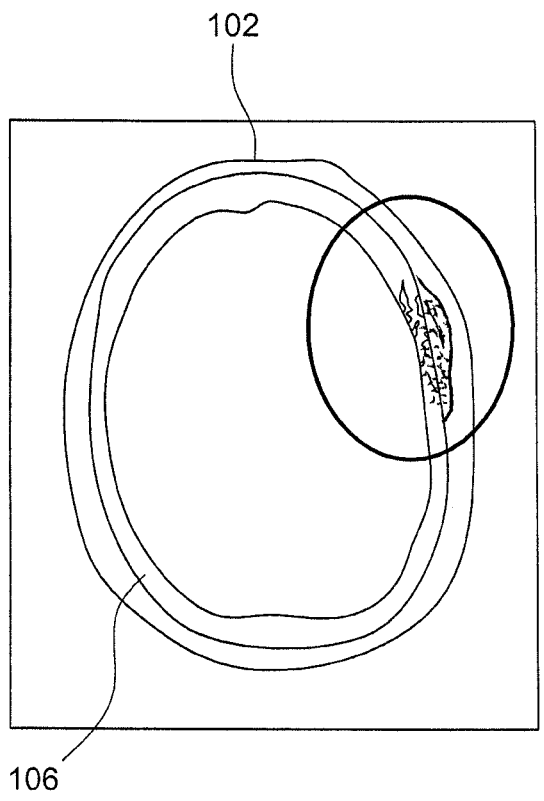
Figure 4B:
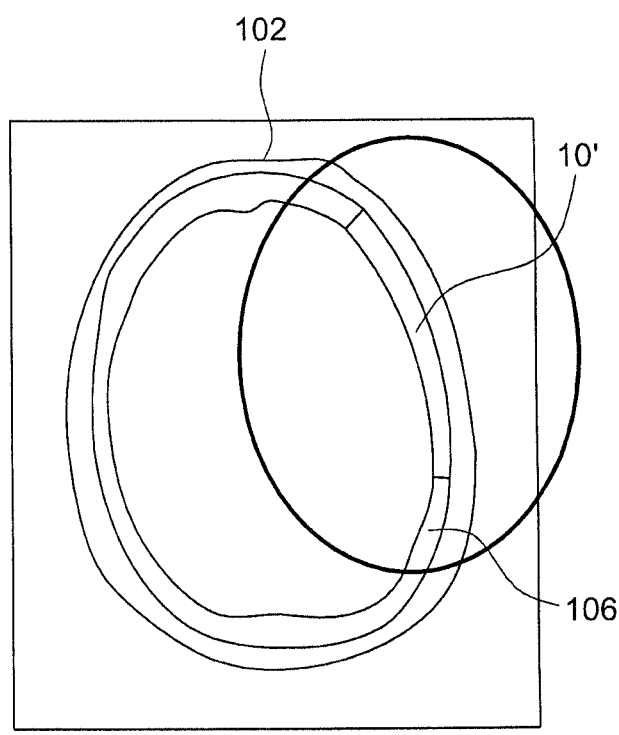

In practice, the method of the present invention includes the following steps: a) identifying a diseased portion associated with the craniofacial anatomy; b) generating and/or accessing a computer-readable reconstruction of a patient's anatomy, such as via a preoperative CT scan that includes an anatomical feature, such as a cranial, craniofacial, and/or facial defect, and constructing a 3D model of the anatomy (see FIG. 4A); c) preselecting a resection area on the model; d) determining implant dimensions (can be a few inches greater than the size of the cranial, craniofacial, and/or facial defect) and prefabricating the clear custom craniofacial implant 10 based upon information generated by preoperative scans (see the prefabricating the clear custom craniofacial implant 10 as shown in FIG. 3C); e) cutting out the diseased portion of the skull or that portion of the skull required to access diseased tissue of the brain or other portion of the anatomy, and thereby creating a cranial, craniofacial, and/or facial defect 100 (see FIGS. 3A and 3B); f) removing the diseased anatomical feature (in addition to step (e), if further necessary); g) positioning the prefabricated clear custom craniofacial implant 10 over the cranial, craniofacial, and/or facial defect 100 created by the removal of the diseased anatomical feature (see FIG. 3C); h) tracing cut lines 12 with a hand-held sterile marker on the prefabricated clear custom craniofacial implant 10 as it lies in-sit over the cranial, craniofacial, and/or facial defect 100 (this advantage being permitted as a result of the clear construction of the craniofacial implant 10 used in accordance with the present invention (see FIG. 3D)); i) cutting the prefabricated clear custom craniofacial implant 10 along the tracing cut lines 12 for optimal fit of the prefabricated clear custom craniofacial implant 10 along the cranial, craniofacial, and/or facial defect 100 and to create the final-size/shape of clear craniofacial implant 10' for exact fit (see FIG. 3E); j) attaching the final clear craniofacial implant 10' to the patient 102 (see FIG. 3G); k) obtaining a post-operative image of the patient 102 and the attached final clear craniofacial implant 10', such as via a CT scan (see FIGS. 4A and 4B respectively showing a pre-operative and post-operative CT scans showing large left sided skull tumor and post-resection views showing ideal symmetry (both bone and soft tissue) and optimal implant location using a clear custom craniofacial implant). Of note, and with reference to FIGS. 4A and 4B, one can see that the bone defect ended up being much larger in size as compared to what one visualizes on pre-operative CT scan—and thus the need for the single-stage cranioplasty method being described here.

It is further appreciated, the method described above could optionally be supplemented with robot assisted technology. For example, and with reference to FIG. 3F, a robotic system 50 could be used to assist the neurosurgical team in the preparation of the prefabricated clear custom craniofacial implant 10. Such a robotic system 50 could include end effectors 52, 54 for interacting with the implant as well as optical sensing mechanisms 56 for visualizing the implant as the robotic system assists in the preparation thereof.

With the exception of steps (g), (h) and (i), the steps associated with the present invention are conventional and variations may be made in accordance with surgical preferences and advancements in medicine. As such, and with reference to FIGS. 3C-3F these steps are described in further detail below. After removing the diseased anatomical feature, the prefabricated clear custom craniofacial implant 10 is prepared for attachment near the healthy portions of the patient's anatomy. In particular, and with the cranial, craniofacial, and/or facial defect 100 open, the surgeon will retrieve the prefabricated clear custom craniofacial implant 10. Based upon, and in consideration of, the unique anatomy of the full-thickness defect within the skull 106 and the outer surface of the skull 106 surrounding the cranial, craniofacial, and/or facial defect 100, the surgeon places the prefabricated clear custom craniofacial implant 10 over and within the space defined by the cranial, craniofacial, and/or facial defect 100 in a desired orientation. Because the prefabricated custom craniofacial implant 10 is "clear", the surgeon is now able (unlike before with the commonly-available, "opaque" implants) to view the periphery 108 of the defect 100 through the prefabricated clear custom craniofacial implant 10 in real-time and uses a sterile intra-operative marking device (for example, a marking pen) 60 to trace the periphery of the cranial, craniofacial, and/or facial defect 100 directly onto the prefabricated clear custom craniofacial implant 10—as opposed to the current day practice of using a hand-made template or cutting guide, or in the future, computer-assisted or robot assisted techniques described by the inventor, Chad R. Gordon. While tracing with a marking device is disclosed in accordance with a preferred embodiment, it is appreciated the creation of the tracing cut lines may be achieved via various other mechanisms for example, etching or otherwise marking the implant.

The surgeon then trims the prefabricated clear custom craniofacial implant 10 along the tracing cut line 12 with an intraoperative contour drill 50. Trimming is achieved using various medical grade tools well known to those skilled in the art, and it is appreciated surgeons will use various trimming techniques depending upon their preferences. Once the prefabricated clear custom craniofacial implant 10 is fully trimmed and has become the final clear craniofacial implant 10', the final clear craniofacial implant 10' is secured to the skull 106 using techniques well known to those skilled in the art providing durable fixation.

The present method exponentially reduces the time necessary for sizing the prefabricated clear custom craniofacial implant 10 relative to the removed bone. The method relies on the use of a fully translucent and clear craniofacial implant 10 and associated techniques for matching the clear craniofacial implant 10 to the cranial, craniofacial, and/or facial defect 100. As described above, single-stage cranioplasties are performed to reconstruct large defects in the skull following removal of unanticipated amounts of cranial bone and/or soft tissue. With this in mind, the present method may be used for reconstructing all craniofacial defects with clear craniofacial implants for an ideal result unlike ever before with improved patient satisfaction, reduced morbidity, lessened risk for bleeding/cerebrospinal fluid leaking, reduced operating room costs, and enhanced patient safety. Accordingly, the present method may be used by all surgeons in performing single-stage cranioplasty following resection of bone disease for which the exact defect size is unknown in advance.

Figure 5:
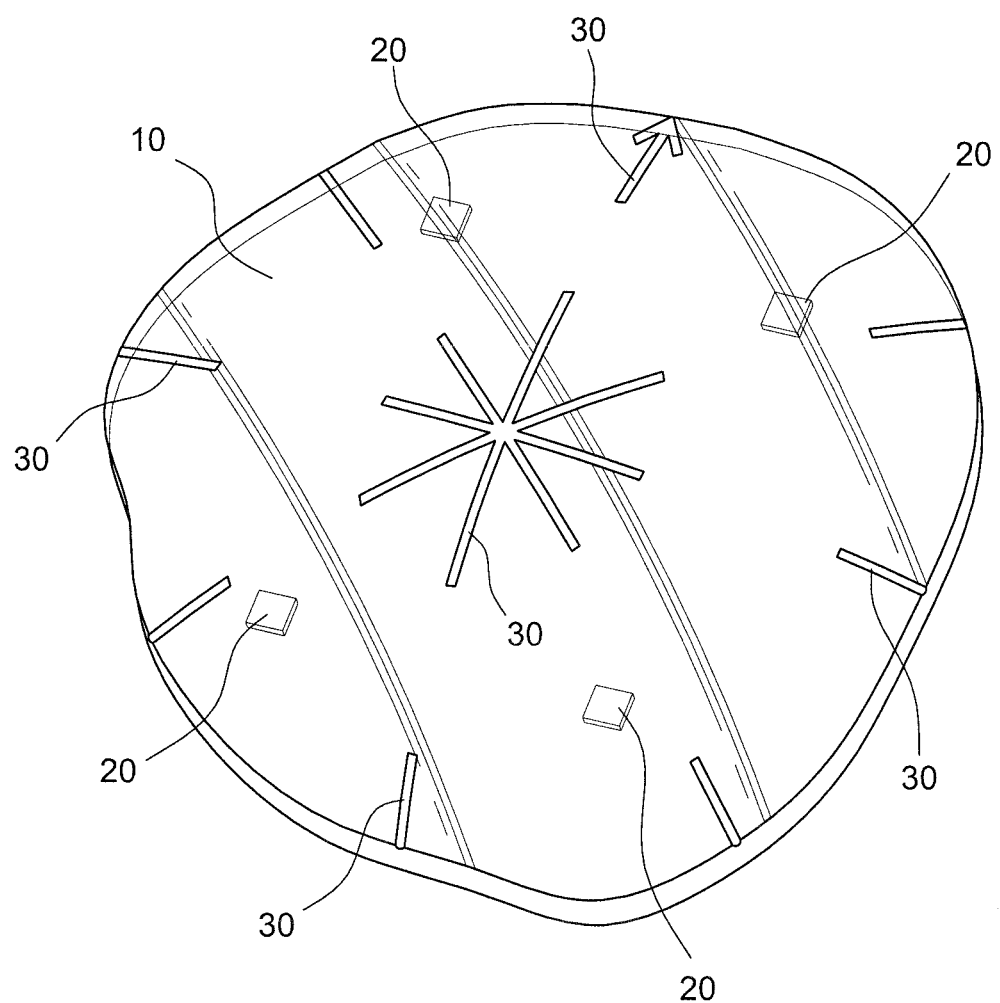
FIG. 5 is a perspective view of an alternate cranial implant in accordance with the present invention using etching marks to assist surgical alignment.

As shown with reference to FIG. 5, and as discussed above, various neurological devices 20, for example, monitoring and treatment devices, such as remote pressure monitor, may also be incorporated within this novel clear implant and are safe from injury during size modification solely due to the translucency and enhanced visibility provided by the clear custom craniofacial implant. The neurological devices incorporated within the clear implant may provide visual monitoring for potential tumor recurrence (i.e., ultrasound, OCT (Optical Coherence Tomography)), may provide battery-powered treatment options for epilepsy (i.e., NeuroPace RNS system), Alzheimer's, or Parkinson's with electricity and/or battery-powered medicinal delivery options with oncological methods such as convection enhanced delivery (CED) and local medicine delivery. Such abilities are preferably achieved using innovative modalities disclosed by Gordon et al. in International Patent Application PCT/US2016/030447, filed May 2, 2017, entitled "LOW PROFILE INTERCRANIAL DEVICE," (published as WO 2017/039762), and U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANUFACTURED THEREBY" (published as U.S. Patent Application Publication No. 2018/0055640), which claims the benefit of U.S. Provisional Patent Application 62/381,242, filed Aug. 30, 2016, entitled "METHOD FOR MANUFACTURING A LOW-PROFILE INTERCRANIAL DEVICE AND THE LOW-PROFILE INTERCRANIAL DEVICE MANUFACTURED THEREBY," all of which are incorporated herein by reference. Further details can be found in the landmark publication by Dr. Gordon and team entitled, "First In-Human Experience With Complete Integration of Neuromodulation Device Within a Customized Cranial Implant," Operative Neurosurgery 2017; 10 (6).

Also, computer-assisted, robot-assisted, and/or surgical methods may be integrated with the use of the clear craniofacial implant as described above. The computer-assisted and/or robot-assisted surgery systems may provide a user enhanced implant reconstruction experience, for example, providing a surgeon unprecedented, immediate visual feedback and allowing single-stage cranioplasty and all related craniomaxillofacial reconstruction for scenarios related to skull neoplasms, etc.—in situations where the tumor defect is not known beforehand, but where a clear custom implant is needed requiring on-table modification via computer-assisted and/or robot-assisted surgery system guidance. Such guidance is preferably achieved using techniques disclosed in U.S. Patent Application Publication No. 2017/0000505, entitled "Computer-Assisted Craniomaxillofacial Surgery," which is incorporated herein by reference. The previously described computer-assisted modality, together with the newfound "clear" implant advantages, may act synergistically moving forward for improved outcomes. Even though the computer-assisted and/or robot-assisted system may provide the guidance as to where modification should occur, the "clear" implant with complete transparency will help the surgeon confirm the efficacy of the computer-assisted and/or robot-assisted system by seeing the skull edges underneath when placed in-situ or, because of enhanced visibility, may obviate the need for additional technologies.

FIGS. 3A-3G, 4A, and 4B illustrate together a representative of the present method for single-stage cranioplasty reconstruction using a clear craniofacial implant 10 and the final result with the embedded final clear craniofacial implant 10'. After generating computer-readable reconstruction of a patient's anatomy, preselecting a resection area on the model, determining implant dimensions (can be a few millimeters greater than the size of the cranial, craniofacial, and/or facial defect), and prefabricating the custom craniofacial implant 10 based upon information generated by known computer-assisted and/or robot-assisted surgical systems, the surgical procedure is initiated with the resection of the skull 106, which leaves behind an anatomical feature of interest, such as a cranial, craniofacial, and/or facial defect 100 with varying thickness which is not consistently smooth due to the manual cutting aspect with craniotomy by a neurosurgeon.

Thereafter, the prefabricated clear custom craniofacial implant 10 is aligned with the unique anatomical features along the periphery 108 of the cranial, craniofacial, and/or facial defect 100 and the prefabricated clear custom craniofacial implant 10 is positioned over the cranial, craniofacial, and/or facial defect 100. The boundaries 108 of the cranial, craniofacial, and/or facial defect 100 are then traced on the prefabricated clear custom craniofacial implant 10 in the form of the tracing cut lines 12 and the prefabricated clear custom craniofacial implant 10 is trimmed in accordance with the tracing cut lines 12 to create the final clear craniofacial implant 10'. Cutting (that is, the cutting of the craniofacial implant 10 to achieve a trimmed craniofacial implant 10 of a desired size and shape) is achieved in a conventional manner using various cutting, sanding and processing machines known to those skilled in the art. It is appreciated that such cutting may include non-manual techniques, for example, as might be performed with computer controlled robotic systems, such as those described by Dr. Gordon's team in U.S. Patent Application Publication No. 2017/0252169, entitled "A Cutting Machine for Resizing New Implants During Surgery," which is incorporated herein by reference. The result of such a single-stage cranioplasty reconstruction according to an embodiment is shown in FIG. 4B with the final clear craniofacial implant 10' attached to the patient's anatomy and showing an exact fit with the absence of gaps along the periphery of the "implant-cranial bone interface." However, future methods for clear implant size modification may include computer-assistance and/or robot-assistance as disclosed in U.S. Patent Application Publication No. 2017/0000505, entitled "Computer-Assisted Craniomaxillofacial Surgery."

Further to the clear craniofacial implant described above, it is appreciated the clear craniofacial implant may be modified in a manner adding even greater functionality without detracting from the ability of a surgeon to advantageously employ the trace lines and cutting described above to achieve an optimal fit. For example, and with reference to FIG. 5, clear craniofacial implant 10 may be provided with laser etching(s) or dyed marking(s) 30 indicating the desired implanted orientation of the clear craniofacial implant (that is, cranial, caudal, left/right lateral) relative to the patient anatomy, or patient specific landmarks. Such etching(s) or marking(s) may be in the form of a compass-shape, diamond, a triangle, a straight-line or any other marking that would be readily understood and identified by a surgeon. The etching(s) or marking(s) could be adapted to a predetermined part of the anatomy, i.e., nasal bone, a suture intersection, etc., wherein the specific anatomy would be determined during the planning stages of the surgical procedure. It is also appreciated etching(s) or marking(s) could be used to identify anatomy beneath the defect, a tumor sight, an aneurysm location, planned integration of other neurological devices, or a functional component (for example, seizure focus, enlarged ventricle with hydrocephalus, shunts, catheters, leads, pumps, drips, flow, etc.), as well as the orientation of such a functional component. For example, the etching(s) or marking(s) could be used in the identification of seizure focus, enlarged ventricle with hydrocephalus, shunts, catheters, leads, pumps, drips, flow, etc. Still further, the etching(s) or marking(s) may be employed on the clear craniofacial implant to identify prescriptions, disease state, date of surgery, type of neurotechnology housed within the implant, etc. It is also appreciated such etching(s) or marking(s) could be used in various combinations to achieve various goals at one time.

It should be appreciated that while both the neurological device(s) 20 and the various etching(s) or marking(s) 30 are shown in FIG. 5 on a single craniofacial implant 10, various combinations of neurological device(s) 20 and/or etching(s)/marking(s) 30 may be used in accordance with the present invention.

Considering the integration of both the neurological device(s) 20 and the various etching(s) or marking(s) 30 into the craniofacial implant 10 in accordance with the present invention, it is contemplated such craniofacial implants may be manufactured in various manners to achieve optimal fit and functionality. In accordance with one embodiment, the neurological device(s) 20 and the various etching(s) or marking(s) 30 are integrated into the body of the craniofacial implant through the use of barium sulfite integrated into craniofacial implants composed of PMMA. In accordance with another embodiment, neurological device(s) 20 and the various etching(s) or marking(s) 30 are integrated into the craniofacial implant 10, for example, through the application of 3D printing (additive manufacturing) techniques with layers or specific areas of radiographic elements or markings incorporated into the structure of the craniofacial implant 10. In accordance with other embodiments, the craniofacial implant 10 may be manufactured through the application of 3D printing, wherein specific shapes adapted for cranial restoration and augmentation are incorporated into the craniofacial implant 10; including, but not limited to, augmentation optimized for the integration of neurological device(s) 20, the provision of etching(s) or marking(s) 30, and/or the surgical integration of other complementary devices. Liquid molding may also be employed, wherein the liquid molding techniques are used to create specific shapes adapted for cranial restoration and augmentation; including, but not limited to, augmentation optimized for the integration of neurological device(s) 20, the provision of etching(s) or marking(s) 30, and/or the surgical integration of other complementary devices. Still further vacuum assisted liquid molding may be employed, wherein vacuum assisted liquid molding techniques are used to create specific shapes adapted for cranial restoration and augmentation; including, but not limited to, augmentation optimized for the integration of neurological device(s) 20, the provision of etching(s) or marking(s) 30, and/or the surgical integration of other complementary devices. Mechanically altered manufacturing methods combining molding, liquid molding, 3D printing may also be used in creating craniofacial implants 10 with specific shapes adapted for cranial restoration and augmentation; including, but not limited to, augmentation optimized for the integration of neurological device(s) 20, the provision of etching(s) or marking(s) 30, and/or the surgical integration of other complementary devices via CNC (Computer Numerical Control) machining, laser, robot, robotic laser. Such craniofacial implants 10 could also be manufactured using milling techniques, wherein blocks of an implant material are milled via CNC machines, laser, robot, and/or robotic laser to create specific shapes adapted for cranial restoration and augmentation; including, but not limited to, augmentation optimized for the integration of neurological device(s) 20, the provision of etching(s) or marking(s) 30, and/or the surgical integration of other complementary devices.

The described methods of the embodiments may be utilized during a surgical procedure, such as a surgical implantation procedure for various forms of craniomaxillofacial surgery and/or neurosurgery including an implant-based cranioplasty. Accordingly, the implant may be a custom, clear craniofacial implant made of either alloplastic biomaterials or biologic tissue engineered cells as described above and a being, such as a human being, on whom the surgical procedure is performed. In other words, the clear craniofacial implant is material-agnostic and only requires complete translucency and optical clarity. The method described above overcomes the deficiencies of the prior art by providing a method that reduces inaccuracies; in particular, performance, stability, simplicity, environmental benefit, cost, etc. When using an opaque implant or bone graft for reconstruction, as used in the prior art, a template may be used to represent the size and shape of the cranial, craniofacial, and/or facial defect—usually paper or cloth from other sterile product in the operating room. When translating the template to the implant orientation changes (anterior, posterior, medial, lateral, superior, inferior, or rotational) occur and the potential for infection and positional rotation increases. Furthermore, the "opaque" nature of the implant prevents the surgeon from seeing the underlying brain and/or skull underneath in relation for size assessment, dural pulsations symbolizing normal brain function, and/or surgical bleeding. These disadvantages have been described and published by the inventor in Gordon C R, et al., "Discussion of Usefulness of an Osteotomy Template for Skull Tumorectomy and Simultaneous Skull Reconstruction," The journal of Craniofacial Surgery, Vol. 27, No. 6, September 2016. Simultaneously each skull or bony skeleton has unique anatomy that implants and/or grafts are contoured to match specifically. The result is that using templates to translate the cranial, craniofacial, and/or facial defect to an "opaque" implant loses orientation and the implant and/or graft does not fit correctly, either the contours don't match with the native skull or the shape is incorrect and requires additional modification. If not using a template, the surgeon is just "eyeballing" the size and shape of the cranial bone defect which requires even more rounds of modification and inferior fit. More importantly, oncological principles are being ignored when using a cutting template.

The ability to directly match up the cranial, craniofacial, and/or facial defect and the implant by using "optically clear" implants for the very first time, in accordance with the present invention, improves orientation and decreases rounds of modification and enhances one's visibility as related to brain or bone bleeding underneath. In addition, because the present method employs a "clear implant" and/or graft—which can be held uniquely over the cranial, craniofacial, and/or facial defect created during surgery—the new size and shape of the cranial, craniofacial, and/or facial defect is more accurately translated to the implant and/or graft; for example, holding the implant over the cranial, craniofacial, and/or facial defect and tracing the cranial, craniofacial, and/or facial defect with a sterile marker. Because the perimeter of the implant rests on the patient's native craniofacial skeleton in the margin between the cranial, craniofacial, and/or facial defect and the edges of the over-sized clear implant, the orientation of the native skull is translated to the implant in a way that was previously impossible when transferring a template from the patient to the current-day implants, which are all "opaque" and provide zero transparency.

In addition to inaccuracy issues, the more accurately the cranial, craniofacial, and/or facial defect can be translated to the implant/graft, the less rounds of modification are required to get an implant/graft to an acceptable size and contour, thereby equating to shortened operative times and minimizing risks for infection and sterility. In fact, traditional methods have demonstrated the need for up to 80 minutes by the inventor Dr. Chad R. Gordon (see Berli J U, et al., "Immediate Single-Stage Cranioplasty Following Calvarial Resection for Benign and Malignant Skull Neoplasms Using Customized Craniofacial Implants," The Journal of Craniofacial Surgery, Vol. 26, No. 5, September 2015). By utilizing the clear custom implant described herein, the operative time can be cut down substantially with improved accuracy for direct translation of cranial, craniofacial, and/or facial defect to implant/graft with much improved speed and efficiency.

Still further, operating rooms average a cost of $62/minute not including anesthesia, salaries, and some other costs (Shippert, R. A Study of Time-Dependent Operating Room Fees and How to Save $100,000 by Using Time-Saving Products. Am J. of Cosmetic Surgery, Vol. 22, No. 1, 2005. Available online July 2013. Macario, A. What does One Minute of Operating Room Time Cost? J. of Clinical Anesthesia, Vol. 22, 2010. Available online July 2013). Shortening surgery by use of a novel clear implant saves money in this setting as well as significant labor.

Ultimately, and considering accuracy is improved, the ideal contour and reconstruction sought by the surgeon and the patient are more achievable with clear implants in single-stage cranioplasty unlike ever before. Further still, it is appreciated the concepts underlying the present invention may be applied to multi-stage cranioplasties, with or without a neurological device being integrated into the clear craniofacial implant. Additionally, the "optical clear" advantage allows unimpeded transmittance of ultrasound and/or wireless ECOG transmission, as reported by Gordon et al. in "First In-human Experience with Complete Integration of Neuromodulation Device Within a Customized Cranial Implant" as discussed above. See also, Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. (anticipated publication 2019)

Figures 6A, 6B:
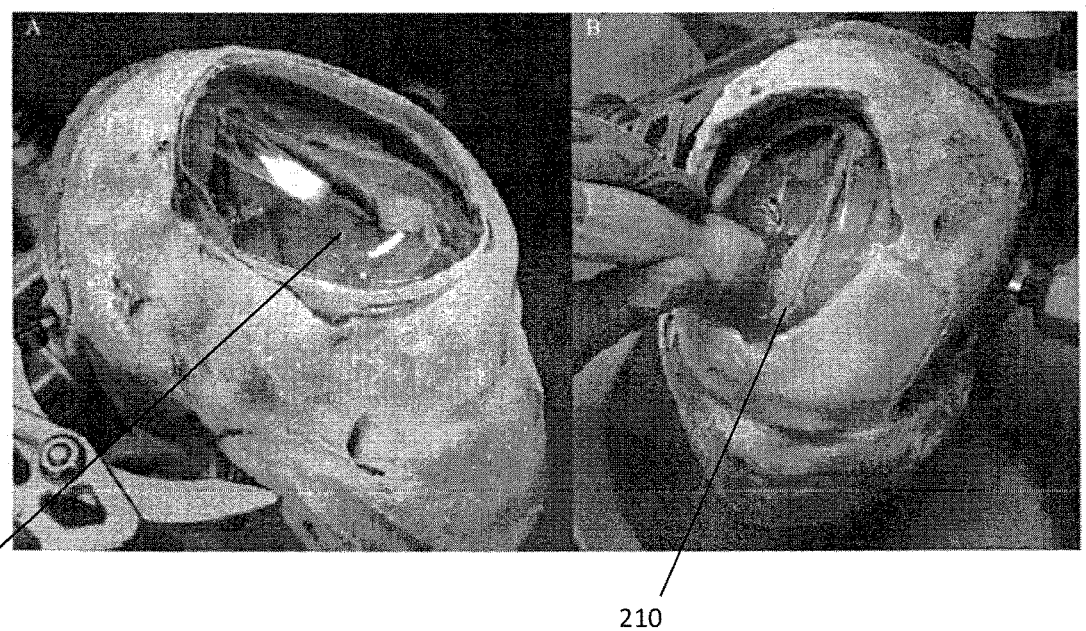
FIGS. 6A and 6B are, respectively, photographs of a clear custom craniofacial implant and craniectomy defect (a) during the reshaping process and (b) with the clear custom craniofacial implant placed within the skull defect, up against the dura.
Figure 7:
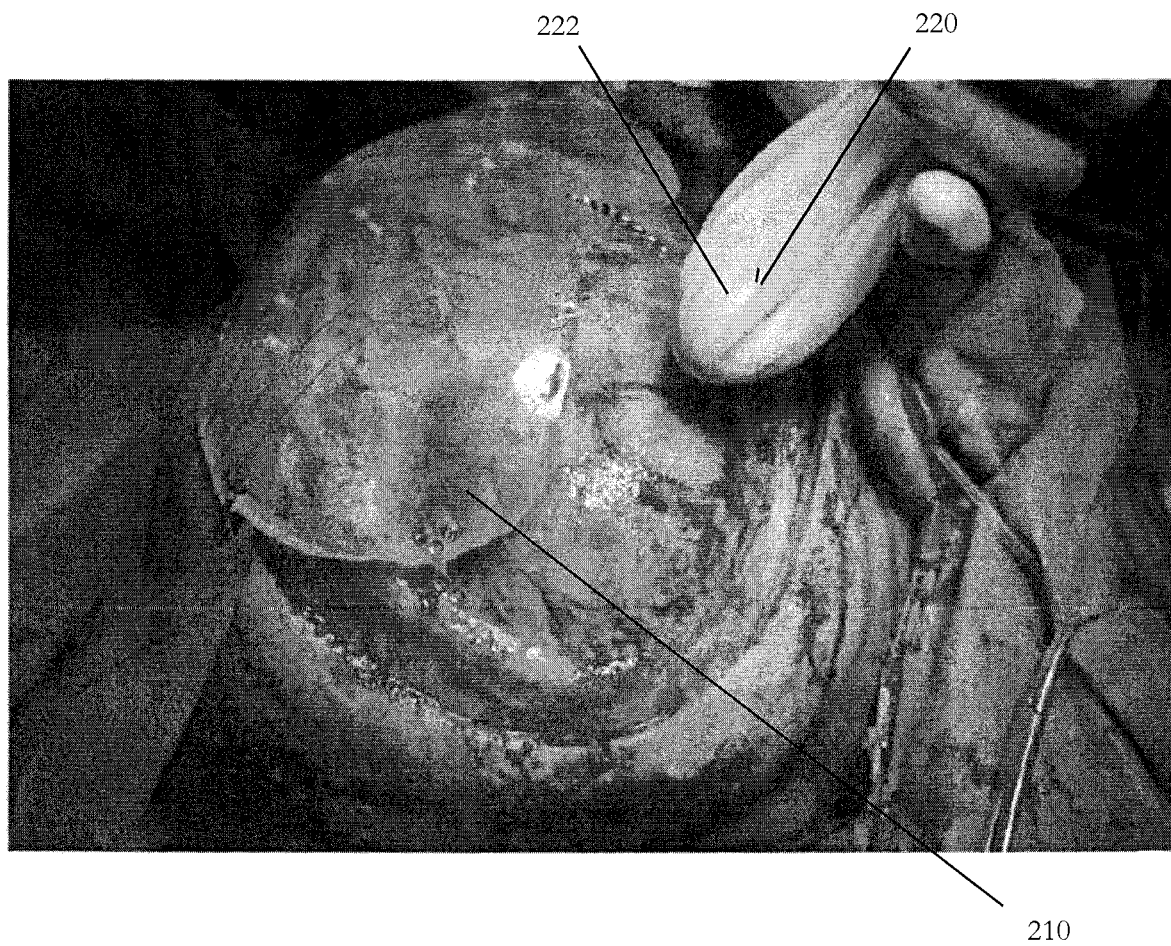
FIG. 7 is a photograph of the skull defect, the clear custom craniofacial implant, and ultrasound transducer within sterile sleeve.

In accordance with an alternate embodiment, and with reference to FIGS. 6A, 6B, and 7, the methodology as presented above may be employed in the use of sonolucent clear custom craniofacial implants 210. As discussed above, the clear custom craniofacial implant 210 of the present invention may be sonolucent allowing passage of ultrasonic sound waves without production of echoes that are due to reflection of some of the waves. Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. (anticipated publication 2019).

Sonographic evaluation of the intracranial contents was previously limited to intraoperative use following bone flap removal, with placement of the ultrasonic transducer directly on the cortical surface or through a trans-sulcal tubular retractor. A clear custom craniofacial implant 210, as described above, with sonolucent characteristics offers a post-operative window into the brain by allowing ultrasound to serve as a bedside imaging modality through the application of trans-cranioplasty ultrasound. By way of example, ultrasound images in accordance with the present invention are obtained using a commercially available transducers and ultrasound systems. It should be appreciated the term "trans-cranioplasty ultrasound," was coined by the inventor, Dr. Chad R. Gordon.

As will be appreciated based upon the following disclosure the clear custom craniofacial implant 210 is preferably composed of clear sonolucent PMMA that allows for both intraoperative and postoperative trans-cranioplasty ultrasound. While clear sonolucent PMMA is disclosed in accordance with a preferred embodiment, it is appreciated other materials, for example, clear sonolucent PEEK, may be used. Through the implementation of intraoperative trans-cranioplasty ultrasound visualization, for example, of recognizable ventricular anatomy, is possible. Furthermore, postoperative bedside trans-cranioplasty ultrasound allows for visualization, for example, of comparable ventricular anatomy and a small epidural fluid collection corresponding to that visualized on an axial computed tomography (CT) scan. Accordingly, the present clear custom craniofacial implant 210 with sonolucent characteristics offers great promise for enhanced diagnostic and therapeutic applications previously limited by cranial bone. Furthermore, the present clear custom craniofacial implant 210 with sonolucent characteristics allows for the possibility of housing implantable devices to provide for real-time surveillance of intracranial pathology.

In accordance with this embodiment, and as briefly discussed above, the clear custom craniofacial implant 210 is preferably composed of clear sonolucent PMMA. The clear custom craniofacial implant 210 has a thickness ranging between 3.0 mm-6.5 mm with a mean thickness of 5.4 mm, which is consistent with native bone flap thickness. The clear custom craniofacial implant 210 also exhibits attenuation characteristics resulting in minimal degradation of the ultrasonic waves generated by the transducer of an ultrasound system.

As those skilled in the art will appreciate, the amplitude change of a decaying plane wave can be expressed as:

$$A = A_0 e^{\alpha d}$$

where, $A_0$ is the unattenuated amplitude of the propagating wave

A is the reduced amplitude after the wave has traveled a distance d

α is the attenuation constant measured in nepers/length (wherein Np/m may be converted to decibels by dividing α by 0.1151), where a neper is a dimensionless quantity e is the exponential (or Napier's constant) which is equal to approximately 2.71828.

It is further appreciated attenuation of an ultrasonic wave is generally a function of the frequency of the ultrasonic wave. With the foregoing in mind the clear custom craniofacial implant has exhibit attenuation of no more than 6 dB/cm at frequencies between 1 MHz and 9 MHz. Within the range of the 2 MHz to 2.5 MHz, the clear custom craniofacial implant exhibits even better (that is, lower) attenuation characteristics. By way of example, attenuation of the skull is commonly considered to be approximately 20 dB/cm at 1 MHz.

As discussed above, the clear custom craniofacial implant 210 of the present invention may be used in conjunction with both intraoperative trans-cranioplasty ultrasound and/or postoperative trans-cranioplasty ultrasound.

Considering first the application of the present invention to intraoperative trans-cranioplasty ultrasound, the clear custom craniofacial implant 210 is implanted as described above. Intraoperative ultrasound images are, thereafter, obtained using a conventional ultrasound system, for example, a 1-5 MHz Philips S5-1 sector array transducer on a Philips EPIQ 7G ultrasound system.

In particular, after fixation of the clear custom craniofacial implant 210 within the resected portion of the skull, and prior to scalp closure, sterile ultrasound gel is applied to the exposed surface of the clear custom craniofacial implant 210, the transducer 220 is placed within a sterile sleeve 222, and the transducer 220 is placed on the clear custom craniofacial implant 210 in a conventional manner. Intraoperative trans-cranioplasty ultrasound is then performed through the clear custom craniofacial implant 210 using the previously mentioned 1-5 MHz sector array transducer (FIG. 7). Following wound closure, sterile ultrasound gel is again applied to the scalp, the transducer 220 is placed on the scalp at the same approximate position, and trans-cranioplasty ultrasound is again performed through the clear custom craniofacial implant 210 using the 1-5 MHz sector array transducer 220. Intraoperative trans-cranioplasty ultrasound (via a 1-5 MHz transducer) results in identification of neuroanatomical structures including the ventricles and choroid plexus.

After surgery, post-operative trans-cranioplasty ultrasound is similarly performed using the same 1-5 MHz Philips S5-1 sector array transducer 220, or a 3-12 MHz Philips L12-3 linear array transducer on a Philips EPIQ 7G ultrasound system.

In particular, the patient's head dressing is removed and sterile ultrasound gel was applied to the scalp, the transducer 220 is placed within a sterile sleeve 222, and the transducer 220 is placed at a position above the clear custom craniofacial implant 210 in a conventional manner. In accordance with a preferred embodiment, images were obtained using both the 1-5 MHz sector array transducer 220 and a 3-12 MHz linear array transducer.

Postoperative trans-cranioplasty ultrasound with a 1-5 MHz sector array transducer 220 provides even greater image clarity than intraoperative trans-cranioplasty ultrasound (most likely because epidural air is absent), demonstrating deep brain parenchyma, ventricles with septum pellucidum, temporal lobes, and hyperechoic temporal fossa skull bone. Additionally, a small epidural collection was revealed using a 3-12 MHz transducer.

With the foregoing in mind, use of a sonolucent clear custom craniofacial implant in accordance with the present invention, permits numerous post-operative, ultrasound-based diagnostic and therapeutic applications including in-clinic assessment of tumor recurrence, cerebral blood flow monitoring, ventricular size measurement for hydrocephalus, midline shift evaluation, non-surgical modulation for movement disorders, recurrent lesion ablation, and targeted drug delivery through blood brain barrier disruption. Furthermore, the sonolucent clear custom craniofacial implant in accordance with the present invention permits therapeutic ultrasound applications previously reliant on MRI guidance such as trans-cranioplasty ultrasound-guided ultrasound ablation. In addition, it is appreciated the clarity of the clear custom craniofacial implant will allow for diagnostic/therapeutic ultrasound devices to be incorporated well within the actual implant itself. It is further appreciated, that trans-cranioplasty ultrasound as achieved in accordance with the present invention may reduce the incidence and cost of post-operative CT scanning by providing a faster, non-ionizing, bedside diagnostic radiographic modality.

Figure 8A:
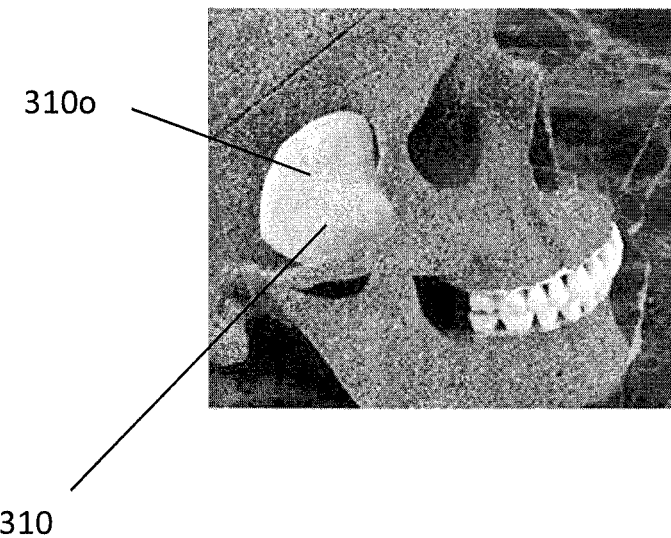
FIGS. 8A, 8B, and 8C show various views of a clear custom craniofacial implant in accordance with an alternate embodiment.

In accordance with one embodiment of the present invention, and as shown with reference to FIG. 8A, it is contemplated the clear custom craniofacial implant 310 of the present invention may be adapted specifically for use in the performance of pterional craniotomies, which, as those skilled in the art will appreciate, are performed at the juncture of the frontal, temporal, greater wing of sphenoid, and parietal bones of the skull.

Figures 8B, 8C:
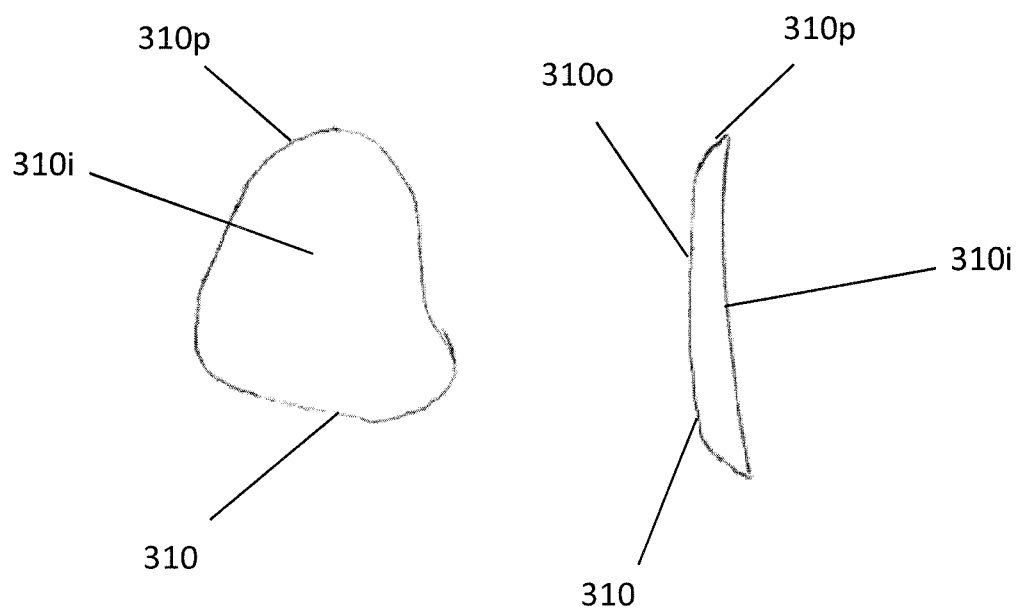

With reference to FIGS. 8A, 8B, and 8C, the clear custom craniofacial implant 310 in accordance with this embodiment includes an outer flat first surface 310o, an inner second surface 310i, and a peripheral edge 310p extending between the outer flat first surface 310o and the inner concave second surface 310i. The provision of an outer flat first surface 310o and an inner curved second surface 310i enhances the ability to obtain ultrasound images through the clear custom craniofacial implant.

In particular, the flat surface defined by the outer flat first surface 310o allows for ideal interaction between the transducer head for optimal optical mating with the window defined by clear custom craniofacial implant 310. In accordance with a preferred embodiment, the outer flat first surface 310o has a surface area of a size to accommodate most commercially available transducers; for example, it has been found that an outer flat first surface 310o with length dimensions of at least 35 mm in both the X and Y directions of the plane in which the outer flat first surface 310o lies is slightly wider than most commercially available transducers. Further still, it is contemplated that the entire outer surface of the clear custom craniofacial implant 310 need not be flat and that a flat central portion (for example, a flat central circle) may be provided to eliminate inconsistency between the transducer and the surface of the clear custom craniofacial implant 310 and to allow optimal viewing even when rotating the transducer.

The inner concave second surface 310i is shaped to maintain contact with the dura for optimizing optical coupling with the dura. With this in mind, and in an effort to ensure contact with the dura is maintained, the clear custom craniofacial implant 310 is constructed with a thickness slightly greater than the thickness of the skull so when the clear custom craniofacial implant 310 is mounted flush with the exterior of the skull it extends a bit into the cranium to assure contact with the dura. As such, the clear custom craniofacial implant 310 has a thickness of preferably 3 mm to 9 mm, preferably, 4 mm to 5 mm. Convex would just be one way to accomplish this. The inner second surface 310i may further be provided with a plurality of rearwardly extending projections that function to assist in compensating for temporal hollowing. The clear custom craniofacial implant 310 is shaped and dimensioned for engagement with the skull of the patient upon implantation in a manner well known to those skilled in the field of neurosurgical procedures.

With the clear custom craniofacial implant 310 positioned in the pterion region along the side of the skull just behind the temple, and in consideration of the clear and sonolucent characteristics thereof, an acoustic window is defined through which the cerebral vasculature, for example, primary arteries, of the brain are accessible for ready imaging.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. An implant, comprising:
a craniofacial implant that is sonolucent and exhibits attenuation of less than 6 dB/cm at frequencies between 1 MHz and 9 MHz, the craniofacial implant being clear with full optical transparency allowing a surgeon to see therethrough and view a cranial, craniofacial, and/or facial defect as well as brain anatomy over which the craniofacial implant is positioned.

2. The implant according to claim 1, wherein the craniofacial implant is a custom craniofacial implant.

3. The implant according to claim 2, wherein the custom craniofacial implant is generated by preoperative scans.

4. The implant according to claim 1, wherein the craniofacial implant is clear PMMA.

5. The implant according to claim 1, wherein the craniofacial implant is shaped and dimensioned for performance of pterional craniotomies.

6. The implant according to claim 1, wherein the craniofacial implant includes an outer flat first surface, an inner second surface, and a peripheral edge extending between the outer flat first surface and the inner second surface, wherein the outer flat first surface allows for ideal interaction between a transducer head for optimal optical mating with the craniofacial implant.

7. The implant according to claim 6, wherein the outer flat first surface has a length of at least 35 mm in both the X and Y directions of a plane in which the outer flat first surface lies so as to be slightly wider than a transducer.

8. The implant according to claim 1, wherein craniofacial implant includes an outer first surface, an inner concave second surface, and a peripheral edge extending between the outer first surface and the inner concave second surface.

9. The implant according to claim 8, wherein the inner concave second surface is shaped to maintain contact with a dura for optimizing optical coupling with the dura.

10. The implant according to claim 1, wherein craniofacial implant includes an outer flat first surface, an inner concave second surface, and a peripheral edge extending between the outer flat first surface and the inner concave second surface.

11. The implant according to claim 10, wherein the inner concave second surface is shaped to maintain contact with a dura for optimizing optical coupling with the dura.

12. The implant according to claim 10, wherein the outer flat first surface has a length of at least 35 mm in both the X and Y directions of a plane in which the outer flat first surface lies so as to be slightly wider than a transducer.

13. The implant according to claim 1, wherein craniofacial implant is sonolucent PEEK.

14. An implant, comprising:
a sonolucent craniofacial implant for cranial, craniofacial, and/or facial defects requiring large-size cranioplasty, the craniofacial implant including an outer flat first surface, an inner curved second surface shaped to maintain contact with a dura for optimizing optical coupling with the dura, and a peripheral edge extending between the outer flat first surface and the inner curved second surface, wherein the outer flat first surface and the inner curved second surface enhance ultrasound images obtained through the craniofacial implant; and
a neurological device incorporated within the craniofacial implant.

15. The implant according to claim 14, wherein the outer flat first surface has a length of at least 35 mm in both the X and Y directions of a plane in which the outer flat first surface lies so as to be slightly wider than a transducer.

16. The implant according to claim 15, wherein the craniofacial implant exhibits attenuation of less than 6 dB/cm at frequencies between 1 MHz and 9 MHz.

17. The implant according to claim 16, wherein the craniofacial implant being clear allowing a surgeon to see therethrough and view a cranial, craniofacial, and/or facial defect as well as brain anatomy over which the craniofacial implant is positioned.

18. The implant according to claim 16, wherein craniofacial implant is clear PMMA.

19. The implant according to claim 14, wherein craniofacial implant is sonolucent PEEK.

20. An implant, comprising:
a craniofacial implant for cranial, craniofacial, and/or facial defects requiring large-size cranioplasty of >25 square centimeters, the craniofacial implant includes polyethylene, polystyrene, acrylic, polyether-ether-ketone (PEEK), or poly(methyl methacrylate), and the craniofacial implant is sonolucent and exhibits attenuation of less than 6 dB/cm at frequencies between 1 MHz and 9 MHz, the craniofacial implant being clear allowing a surgeon to see therethrough and view a cranial, craniofacial, and/or facial defect as well as brain anatomy over which the craniofacial implant is positioned; and
a neurological device incorporated within the craniofacial implant.

21. An implant, comprising:
a sonolucent custom craniofacial implant for cranial, craniofacial, and/or facial defects requiring large-size cranioplasty of >25 square centimeters, the craniofacial implant includes polyethylene, polystyrene, acrylic, polyether-ether-ketone (PEEK), or poly(methyl methacrylate) and the craniofacial implant also includes an outer flat first surface having a length of at least 35 mm in both the X and Y directions for the purpose of allowing for ideal interaction between a transducer head and the craniofacial implant, an inner second surface concave shaped to maintain contact with a dura for optimizing optical coupling with the dura, and a peripheral edge extending between the outer flat first surface and the inner second surface, wherein the outer flat first surface and the inner curved second surface enhance ultrasound images obtained through the craniofacial implant.

* * * * *